United States Patent [19]
Shigemori et al.

[11] Patent Number: 5,858,800
[45] Date of Patent: Jan. 12, 1999

[54] OPTICAL MEASUREMENT METHOD AND APPARATUS THEREOF

[76] Inventors: Kazuhisa Shigemori; Kenji Masuda, both c/o Daikin Industries, Ltd., Shiga-seisakusho, 1000-2, Aza Ootani, Okamoto-cho, Kusatsu-shi, Shiga 525, Japan

[21] Appl. No.: 586,876

[22] PCT Filed: May 25, 1995

[86] PCT No.: PCT/JP95/01010

§ 371 Date: Mar. 22, 1996

§ 102(e) Date: Mar. 22, 1996

[87] PCT Pub. No.: WO95/32417

PCT Pub. Date: Nov. 30, 1995

[30] Foreign Application Priority Data

May 25, 1994 [JP] Japan .................................. 6-111600

[51] Int. Cl.$^6$ ................ G01N 33/534; G01N 33/552
[52] U.S. Cl. ............... 436/518; 356/317; 356/318; 356/244; 356/246; 385/12; 385/129; 385/130; 422/57; 422/58; 422/82.05; 422/82.08; 422/82.11; 435/287.1; 435/287.2; 435/288.7; 435/808; 436/164; 436/165; 436/172; 436/527; 436/805
[58] Field of Search ................ 385/12, 129, 130; 356/317, 318, 244, 246; 422/57, 58, 82.05, 82.08, 82.11; 435/287.1, 287.2, 288.7, 808; 436/164, 165, 172, 518, 527, 805

[56] References Cited

U.S. PATENT DOCUMENTS

| | | | |
|---|---|---|---|
| 4,810,658 | 3/1989 | Shanks et al. | 436/172 |
| 4,818,710 | 4/1989 | Sutherland et al. | 436/527 |
| 4,857,273 | 8/1989 | Stewart | 422/68 |
| 4,978,503 | 12/1990 | Shanks et al. | 422/58 |
| 5,512,492 | 4/1996 | Herron et al. | 436/518 |
| 5,538,850 | 7/1996 | King et al. | 435/6 |

FOREIGN PATENT DOCUMENTS

| | | |
|---|---|---|
| 56-22938 | 3/1981 | Japan . |
| 61-077745 | 4/1986 | Japan . |
| 61-226644 | 10/1986 | Japan . |
| 3-37552 | 2/1991 | Japan . |
| 6-117997 | 4/1994 | Japan . |

*Primary Examiner*—Christopher L. Chin
*Attorney, Agent, or Firm*—Beveridge, DeGrandi, Weilacher & Young, L.L.P.

[57] ABSTRACT

An exciting light 2 is introduced within a slab-type optical waveguide 1, an evanescent wave due to the exciting light 2 excites fluorescent light, and among the fluorescent light, a fluorescent light which is radiated in a direction which direction crosses the exciting light 2 by a predetermined angle, is detected by a fluorescent light detector 4. Consequently, the exciting light and the fluorescent light are spacially separated so as to reduce stray light, and an arrangement of an optical system is simplified.

19 Claims, 14 Drawing Sheets

DISTANCE (mm)

WAVEGUIDE DISTANCE (mm)

OPTICAL MEASUREMENT METHOD AND APPARATUS THEREOF

TECHNICAL FIELD

The present invention relates to an optical measurement method and apparatus thereof, and more particularly to an optical measurement method and apparatus thereof which are suitable to cases. One of the cases is a case which introduces an exciting light into a slab-type optical waveguide, propagates the exciting light within the slab-type optical waveguide in a total reflection manner so as to generate an evanescent wave component, excites fluorescent substance by the evanescent wave component which fluorescent substance exist in vicinity of a face of the slab-type optical waveguide which face totally reflects the exciting light, and detects a fluorescent light component by a detector which fluorescent light is a part of the generated fluorescent light and is introduced into the slab-type optical waveguide through the face and is outgone from the slab-type optical waveguide thereafter. The other of the cases is a case which introduces an exciting light into a total reflection prism, totally reflects the exciting light by a total reflection face of the total reflection prism so as to generate an evanescent wave component, excites fluorescent substance by the evanescent wave component which fluorescent substance exist in vicinity of the total reflection face, and detects a fluorescent light component by a detector which fluorescent light is a part of the generated fluorescent light and is introduced into the total reflection prism through the total reflection face and is outgone from the total reflection prism thereafter.

BACKGROUND ART

From past, a method is proposed which introduces an exciting light into a slab-type optical waveguide, propagates the exciting light within the slab-type optical waveguide in a total reflection manner so as to generate an evanescent wave component, excites fluorescent substance by the evanescent wave component which fluorescent substance exist in vicinity of a face of the slab-type optical waveguide which face totally reflects the exciting light, and detects a fluorescent light component by a detector which fluorescent light is a part of the generated fluorescent light and is introduced into the slab-type optical waveguide through the face and is outgone from the slab-type optical waveguide thereafter. When a light propagating within a medium having a larger refractive index totally reflects at a boundary face of the medium and a medium having a smaller refractive index, the evanescent wave is a light component which exist within the medium having smaller refractive index and within a limited region with respect to the boundary face. Specifically, when is is supposed that refractive indexes of the medium are $n1$, $n2$ (where $n1<n2$), a wavelength of the light is $\lambda$, a incident angle is $\theta$, an intensity of an incident light is $I0$, an intensity of a light at a point which is apart from the boundary face by a distance $z$ is $I$, a specific refractive index is $n$ ($=n2/n1$), a distance of a point from the boundary face (invasion depth) is $dp$ which point makes an electric field strength to be $1/e$ of that of the boundary face of the optical waveguide. The intensity $I$ depends upon the distance $Z$ and is expressed with equation (1).

$$I=I0\{4n^2/(n^2-1)\}\cos^2\theta\exp(-2z/dp)$$

$$dp=\lambda/[2\pi\{(n2^2/n1^2)\sin^2\theta-1\}^{1/2}] \quad (1)$$

Therefore, it is understood by analyzing the equation (1) that an evanescent wave exists within a limited region with respect to the boundary face (refer tp M. Born & E. Wolf "Principle Of Optics I"). Wherein, it is assumed that the incident angle $\theta$ is greater than a critical angle $\theta c$ $\{\theta c=\sin^{-1}(n1/n2)\}$.

As to evanescent wave, not only penetrating of a light to lower refractive index side but also propagating of a light from lower refractive index side to higher refractive index side satisfy the foregoing. That is, a rate of a light which propagates to fluorescence dye et al. by an angle which is greater than the critical angle is expressed with the equation (1) similarly, which fluorescent dye et al. exists at a position apart from the boundary face by a distance $z$. Therefore, only light which is generated at vicinity of the boundary face can propagates to the medium having the higher refractive index by an angle which is greater than the critical angle {refer to C. K. Carniglia et. al. "J. Opt. Soc. Am. 62, 479 (1979)}.

It is a phenomenon that evanescent wave exists localized in a region which is near a boundary face and is an extent of nearly wavelength, therefore evanescent wave is possibly applied as a probe light for detecting boundary phenomena. In application to fluoresence immuno assay, determination of reagent labeled with fluorescence dye which dye is bound at a surface of solid phase by antigen-antibody reaction, is possibly performed by directly measuring fluorescent light without separating and washing out unreacted reagent which exist freely within a test liquid.

Following three methods are known as fluorescence immuno assay using above-mentioned evanescent light.

(1) exciting fluorescence dye with evanescent light which dye is bound to a face by immuno-reaction which face is a face of an optical waveguide for totally reflecting an exciting light, and detecting a fluorescent light component by a detector which fluorescent light is a part of fluorescent light radiated from excited fluorescence dye and is intruded into the optical waveguide through the face and is radiated almost uniformly from a face which is opposite to the fluorescent light incidenting face of the optical waveguide as a plane wave thereafter (refer to FIG. 24 and U.S. Pat. No. 3,604,927).

(2) exciting fluorescence dye uniformly using a plane wave, utilizing characteristics in which only fluorescent light from fluorescence dye which are bound to a surface of an optical waveguide, intrudes within the optical waveguide and the fluorescent light propagates within the optical waveguide, and detecting fluorescent light which is outgone from an egde section of the optical waveguide which egde section is located in fluorescent light propagating direction (refer to FIG. 25 and Japanese Patent Laid Open Tokuhyoushou 61-502418), and (3) exciting fluorescence dye with evanescent light which dye is bound to a face by immuno-reaction which face is a face of an optical waveguide for totally reflecting an exciting light, and detecting a fluorescent light component by a detector which fluorescent light is a part of fluorescent light radiated from fluorescence dye bound to the surface of the optical waveguide and is intruded into the optical waveguide and is propagated within the optical waveguide in a total reflection manner and is outgone from the optical waveguide optical axis of which fluorescent light coincident with that of exciting light (refer to FIG. 26 and Japanese Patent Laid Open Tokuhyoushou 59-501873).

PROBLEMS TO BE SOLVED BY THE INVENTION

When the method (1) is employed, total radiating quantity of fluorescent light is great. But, it is difficult to catch fluorescent light which is uniformly radiated from a wide area with wide radiating angle. Therefore, detectable quantity of fluorescent light is limited in real. Further, when exciting light is scattered due to fine flaw, insufficient surface roughness and the like of the optical waveguide, fluorescence dye within unreacted reagent is excited by the scattered exciting light which fluorescence dye is far apart from the surface of the optical waveguide so that a great offset of fluorescent signal is generated. The offset is regulated by surface irregularity of the optical waveguide, therefore it is difficult to control the offset exactly.

When the method (2) is employed, a plane light is employed as an exciting light, and the exciting light is almost uniformly irradiated from perpendicular direction with respect to a surface of the optical waveguide so that a difficult is eliminated that exciting light is converged and incident within the optical waveguide. But, mixing of fluorescent light from unreacted fluorescence dye or exciting light to some degree to fluorescent light which is a signal light, cannot be avoided due to surface irregularity of the optical waveguide. Further, a light source with great quantity of light is required for irradiating exciting light to a wide area with sufficient quantity of light.

When the method (3) is employed, exciting light itself exist localized at boundary face, and only fluorescent light from fluorescence dye intrudes within the optical waveguide which fluorescence dye is bound in vicinity of the boundary face, and the intruded fluorescent light propagates within the optical waveguide in a total reflection manner, therefore double filtering is applied spacially against a noise. For example, when the optical waveguide has surface irregularity, influence depending upon mixing scattered exciting light to signal light is extremely smaller than that of the method (2). Also, a quantity of fluorescent light which is caused by scattered exciting light and is propagated within the optical waveguide, is extremely smaller than fluorescent light excited by scattered exciting light which fluorescent light is a problem in the method (1). Therefore, this method is most suitable for measurement with high sensitivity.

When measurement is carried out using the method (3), conventionally a method is employed for detecting fluorescent light which is extremely weak in usual, which method is a method to detect fluorescent light which is outgone from the exciting light incidenting edge side of the optical waveguide which edge side is influenced by the exciting light little. In this case, an optical axis of the exciting light and an optical axis of the fluorescent light coincident to one another, therefore it is necessary to separate the optical axis of the exciting light and the optical axis of the fluorescent light using a half mirror, dichroic mirror which is more preferable, and the like. Specifically, as is illustrated in FIG. 17, an exciting light outgone from a exciting light source 100 such as a semiconductor laser and the like is guided to a dichroic mirror 104 through a collimator lens 101, a filter 102 for controlling quantity of light when it is required, and a cylindrical face lens 103. The exciting light is reflected by the dichroic mirror 104 and is incident to a slab-type optical waveguide 106 which optical waveguide 106 and a reaction vessel 105 in which antigen-antibody reaction is carried out, are made in one body. And, a fluorescent light outgone from the slab-type optical waveguide 106 is guided to a detector 109 such as a photomultiplier through the dichroic mirror 104, a converging lens 107 which comprises a pair of convex lenses, ans a sharp cut filter 108 for eliminating the exciting light. When such arrangement is employed, a light path of the exciting light from the dichroic mirror 104 to the slab-type optical waveguide 106 is included within a viewfield of the detector 109 inevitably. Therefore, optical parts causing reflection, scattering of the exciting light, causing scattering due to dust, splash and the like cannot be disposed between the dichroic mirror 104 and the slab-type optical waveguide 106. The optical parts are exemplified as optical parts and the like which are disposed in vertical with respect to the optical axis such as lens, filter and the like.

Therefore, the exciting light should sufficiently be focused so as to incident the exciting light into the slab-type optical waveguide 106. And, a light lens should be employed so as to detect fluorescent light outgone from the slab-type optical waveguide by an extent of an angle to some degree. But, the lens is to disposed prior to the dichroic mirror 104 with respect to the exciting light source 100 or the detector 109 by taking the above limitation into consideration so that the optical system is increased in size.

When the exciting light is not incident accurately into the slab-type optical waveguide 106 (for example, when the exciting light irradiates to an edge of the exciting light indidenting edge of the slab-type optical waveguide 106), the exciting light leaks into the reaction vessel so as to excite unreacted labeled reagent or so as to propagates the exiting light within the slab-type optical waveguide 106 by an angle which is different from a designed angle. Therefore, a laser beam should be incident into the slab-type optical waveguide 106 which laser beam is accurately aligned with respect to the slab-type optical waveguide 106 and has small aberration and a small spot size. When the laser beam which is focused to such a small region is incident as the exiting light into the slab-type optical waveguide 106, an energy density is too great so as to degrade the fluorescence dye due to light. Therefore, when the intensity of the exiting light should not be lowered and the degradation of the fluorescence dye should be prevented, a focusing point of the laser beam should be shifted to rear side to some degree with respect to the exiting light incidenting face of the slab-type optical waveguide 106 so as to contact a light to the fluorescence dye which light is expanded to some degree. In this case, expanded laser beam should be incident into the slab-type optical waveguide 106 under a condition that the expanded laser beam should not irradiates the edge of the exiting light incidenting edge of the slab-type optical waveguide 106, therefore margin for positioning is decreased. By taking those points into consideration, demand for characteristics of the lens and the like becomes severed, and load for adjustment and the like is increased so that cost is inevitably increased.

Further, the energy density of the laser beam is extremely high until the laser beam incident into the slab-type optical waveguide 106 is expanded to some degree, so that fluorescence dye bound to a region at which the energy density of the laser beam is extremely high is degraded which fluorescence dye is a part of fluorescence dye which is bound to a surface of the slab-type optical waveguide 106. When fluorescence dye is degraded, fluorescent light corresponding to the degraded fluorescence dye is not generated or is decreased so as to lower accuracy in optical measurement.

DISCLOSURE OF THE INVENTION

The present invention was made in view of the above problems.

It is a first object of the present invention to offer a optical measurement method and apparatus thereof which improve sensitivity and accuracy by decreasing influence of reflection and scattering of an exiting light, and achieving simplification and decreasing in size of an optical system.

It is a second object of the present invention to offer an optical measurement method and apparatus thereof which softens demand for characteristics of lens and the like, and suppresses increase in cost to great degree by decreasing load for adjustment and the like.

It is a third object of the present invention to offer an optical measurement method and apparatus thereof which suppresses lowering in optical measurement accuracy due to degradation of fluorescence dye even when an energy density of an exciting light is great.

It is a fourth object of the present invention to offer an optical measurement method and apparatus thereof which increases a quantity of detectable fluorescent light among fluorescent light which propagates within the slab-type optical waveguide and outgoes thereafter.

An optical measurement method according to claim 1 is a method which introduces an exciting light into a slab-type optical waveguide, propagates the exciting light within the slab-type optical waveguide in a total reflection manner so as to generate an evanescent wave component, excites fluorescent substance by the evanescent wave component which fluorescent substance exist in vicinity of a face of the slab-type optical waveguide which face totally reflects the exciting light, and detects an excited fluorescent light. The method detects a fluorescent light component among the excited fluorescent light by the evanescent light component which fluorescent light component once incidents into the slab-type optical waveguide through a face which totally reflects the exciting light, and propagates to an edge face of the slab-type optical waveguide which has predetermined relative angles with respect to an exciting light incidenting face, an exciting light outgoing face and the face which totally reflects the exiting light.

In claim 1 and following claims, the predetermined relative angles are 45°–135° sufficiently. They are 90° preferably.

As to the optical measurement method according to claim 1, the method introduces an exciting light into the slab-type optical waveguide, propagates the exciting light within the slab-type optical waveguide in a total reflection manner so as to generate an evanescent wave component, excites fluorescent substance by the evanescent wave component which fluorescent substance exist in vicinity of the face of the slab-type optical waveguide which face totally reflects the exciting light, and detects an excited fluorescent light. When the method carries out the above operation, the method detects a fluorescent light component among the excited fluorescent light by the evanescent light component which fluorescent light component once incidents into the slab-type optical waveguide through the face which totally reflects the exciting light, and propagates to the edge face of the slab-type optical waveguide which has predetermined relative angles with respect to the exciting light incidenting face, the exciting light outgoing face and the face which totally reflects the exiting light. Therefore, no optical members for separating the exiting light and the fluorescent light as the signal light is required. Further, influence of reflection and scattering by optical elements to the fluorescent light which is to be detected, is greatly suppressed because no overlapping portion exist of the exiting light and the fluorescent light as the signal light. Therefore, a lens can be disposed at neighbouring position with respect to the slab-type optical waveguide, a lens having a shorter focal distance can be employed, so that the optical system is decreased in size. Furthermore, freedom in disposition of the optical system for optical measurement with respect to the slab-type optical waveguide and freedom of disposition of the optical elements included within the optical system are greatly raised, and a countermeasure against soil of the optical elements. Further, the optical measurement signal is increased by increasing a number of detectors which detect the fluorescent light component. Furthermore, the fluorescent light component is detected within a wide extent by lengthening the length of the slab-type optical waveguide which length is a length in a propagating direction of the exciting light, so that the optical measurement signal is increased.

An optical measurement method according to claim 2 is a method which introduces an exciting light into a total reflection prism, totally reflects the exciting light by a total reflection face of the total reflection prism so as to generate an evanescent wave component, excites fluorescent substance by the evanescent wave component which fluorescent substance exist in vicinity of the total reflection face, and detects an excited fluorescent light component. The method detects the fluorescent light component which is a part of the generated fluorescent light, is introduced into the total reflection prism through the total reflection face, and propagates to an edge face of the total reflection prism which has predetermined relative angles with respect to an exciting light incidenting face, an exciting light outgoing face and the face which totally reflects the exiting light.

As to the optical measurement method according to claim 2, the method introduces an exciting light into the total reflection prism, totally reflects the exciting light by the total reflection face of the total reflection prism so as to generate an evanescent wave component, excites fluorescent substance by the evanescent wave component which fluorescent substance exist in vicinity of the total reflection face, and detects an excited fluorescent light component. When the method carries out the above operation, the method detects the fluorescent light component which is a part of the generated fluorescent light, is introduced into the total reflection prism through the total reflection face, and propagates to the edge face of the total reflection prism which has predetermined relative angles with respect to the exciting light incidenting face, the exciting light outgoing face and the face which totally reflects the exiting light. Therefore, no optical members for separating the exiting light and the fluorescent light as the signal light is required. Further, influence of reflection and scattering by optical elements to the fluorescent light which is to be detected, is greatly suppressed because no overlapping portion exist of the exiting light and the fluorescent light as the signal light. Therefore, a lens can be disposed at neighbouring position with respect to the slab-type optical waveguide, a lens having a shorter focal distance can be employed, so that the optical system is decreased in size. Furthermore, freedom in disposition of the optical system for optical measurement with respect to the slab-type optical waveguide and freedom of disposition of the optical elements included within the optical system are greatly raised, and a countermeasure against soil of the optical elements. Further, the optical measurement signal is increased by increasing a number of detectors which detect the fluorescent light component.

An optical measurement method according to claim 3 is a method which screens a portion of the edge face from a viewfield of the fluorescent light component detector which portion corresponds to a region in which an energy of the exciting light is great.

As to the optical measurement method according to claim 3, the portion of the edge face is screened from the viewfield of the fluorescent light component detector which portion corresponds to the region in which an energy of the exciting light is great. Therefore, influence of degraded fluorescent substance to the optical measurement result is prevented from occurence nevertheless of degrading of the fluorescent substance due to the great energy of the exiting light. Further, it is not required that the energy of the exciting light is determined to be lower so as not to degrade the fluorescent substance, therefore the exciting light is sufficiently focused and incident into the slab-type optical waveguide so that a sufficient margin for disposition is obtained. Furthermore, demand for characteristics of lens and the like is softened, and load of adjustment and the like is decreased so that cost down is realized. Further, tolerance is softened which is required for the slab-type optical waveguide. Furthermore, optical measurement accuracy is improved because the energy of exciting light can be increased. Further, as the softening of the demand for characteristics of lens and the like, when a dark lens is employed and the exciting light is incident into the slab-type optical waveguide as a narrow beam, for example, influence of inuniformity is greatly suppressed. Further, no cylindrical face lens is required, therefor an arrangement for carrying out optical measurement is simplified so that cost down is realized from the point of view.

An optical measurement apparatus according to claim 4 is an apparatus which introduces an exciting light into a total reflection prism, totally reflects the exciting light by a total reflection face of the total reflection prism so as to generate an evanescent wave component, excites fluorescent substance by the evanescent wave component which fluorescent substance exist in vicinity of the total reflection face, and detects an excited fluorescent light component. The apparatus includes a detector which detects the fluorescent light component which is a part of the generated fluorescent light, is introduced into the total reflection prism through the total reflection face, and propagates to an edge face of the total reflection prism which has predetermined relative angles with respect to an exciting light incidenting face, an exciting light outgoing face and the face which totally reflects the exiting light.

As to the optical measurement apparatus according to claim 4, the apparatus introduces an exciting light into the total reflection prism, totally reflects the exciting light by the total reflection face of the total reflection prism so as to generate an evanescent wave component, excites fluorescent substance by the evanescent wave component which fluorescent substance exist in vicinity of the total reflection face, and detects an excited fluorescent light component. When the apparatus carries out the above operation, the apparatus includes the detector which detects the fluorescent light component which is a part of the generated fluorescent light, is introduced into the total reflection prism through the total reflection face, and propagates to the edge face of the total reflection prism which has predetermined relative angles with respect to the exciting light incidenting face, the exciting light outgoing face and the face which totally reflects the exiting light. Therefore, no optical members for separating the exiting light and the fluorescent light as the signal light is required. Further, influence of reflection and scattering by optical elements to the fluorescent light which is to be detected, is greatly suppressed because no overlapping portion exist of the exiting light and the fluorescent light as the signal light. Therefore, a lens can be disposed at neighbouring position with respect to the slab-type optical waveguide, a lens having a shorter focal distance can be employed, so that the optical system is decreased in size. Furthermore, freedom in disposition of the optical system for optical measurement with respect to the slab-type optical waveguide and freedom of disposition of the optical elements included within the optical system are greatly raised, and a countermeasure against soil of the optical elements. Further, the optical measurement signal is increased by increasing a number of detectors which detect the fluorescent light component.

An optical measurement apparatus according to claim 5 is an apparatus which introduces an exciting light into a slab-type optical waveguide, propagates the exciting light within the slab-type optical waveguide in a total reflection manner so as to generate an evanescent wave component, excites fluorescent substance by the evanescent wave component which fluorescent substance exist in vicinity of a face of the slab-type optical waveguide which face totally reflects the exciting light, and detects an excited fluorescent light. The apparatus includes a detector which detects a fluorescent light component among the excited fluorescent light by the evanescent light component which fluorescent light component once incidents into the slab-type optical waveguide through a face which totally reflects the exciting light, and propagates to an edge face of the slab-type optical waveguide which has predetermined relative angles with respect to an exciting light incidenting face, an exciting light outgoing face and the face which totally reflects the exciting light.

As to the optical measurement apparatus according to claim 5, the apparatus introduces an exciting light into the slab-type optical waveguide, propagates the exciting light within the slab-type optical waveguide in a total reflection manner so as to generate an evanescent wave component, excites fluorescent substance by the evanescent wave component which fluorescent substance exist in vicinity of the face of the slab-type optical waveguide which face totally reflects the exciting light, and detects an excited fluorescent light. When the apparatus carries out the above operation, the apparatus includes the detector which detects a fluorescent light component among the excited fluorescent light by the evanescent light component which fluorescent light component once incidents into the slab-type optical waveguide through the face which totally reflects the exciting light, and propagates to the edge face of the slab-type optical waveguide which has predetermined relative angles with respect to the exciting light incidenting face, the exciting light outgoing face and the face which totally reflects the exiting light. Therefore, no optical members for separating the exiting light and the fluorescent light as the signal light is required. Further, influence of reflection and scattering by optical elements to the fluorescent light which is to be detected, is greatly suppressed because no overlapping portion exist of the exiting light and the fluorescent light as the signal light. Therefore, a lens can be disposed at neighbouring position with respect to the slab-type optical waveguide, a lens having a shorter focal distance can be employed, so that the optical system is decreased in size. Furthermore, freedom in disposition of the optical system for optical measurement with respect to the slab-type optical waveguide and freedom of disposition of the optical elements included within the optical system are greatly raised, and a countermeasure against soil of the optical elements. Further, the optical measurement signal is increased by increasing a number of detectors which detect the fluorescent light component. Furthermore, the fluorescent light component is detected within a wide extent by lengthening the length of the slab-type optical waveguide which length is a length in a propagating direction of the exciting light, so that the optical measurement signal is increased.

An optical measurement apparatus according to claim 6 is an apparatus which screens a portion of the edge face from a viewfield of the fluorescent light component detector which portion corresponds to a region in which an energy of the exciting light is great.

As to the optical measurement apparatus according to claim 6, the portion of the edge face is screened from the viewfield of the fluorescent light component detector which portion corresponds to the region in which an energy of the exciting light is great. Therefore, influence of degraded fluorescent substance to the optical measurement result is prevented from occurence nevertheless of degrading of the fluorescent substance due to the great energy of the exiting light. Further, it is not required that the energy of the exciting light is determined to be lower so as not to degrade the fluorescent substance, therefore the exciting light is sufficiently focused and incident into the slab-type optical waveguide so that a sufficient margin for disposition is obtained. Furthermore, demand for characteristics of lens and the like is softened, and load of adjustment and the like is decreased so that cost down is realized. Further, tolerance is softened which is required for the slab-type optical waveguide. Furthermore, optical measurement accuracy is improved because the energy of exciting light can be increased. Further, as the softening of the demand for characteristics of lens and the like, when a dark lens is employed and the exciting light is incident into the slab-type optical waveguide as a narrow beam, for example, influence of inuniformity is greatly suppressed. Further, no cylindrical face lens is required, therefor an arrangement for carrying out optical measurement is simplified so that cost down is realized from the point of view.

An optical measurement apparatus according to claim 7 is an apparatus in which a reaction vessel is formed by plural wall members one of which is a slab-type optical waveguide which totally reflects an exciting light, the slab-type optical waveguide is lengthened to exciting light incidenting side from the reaction vessel, and a thickness of the slab-type optical waveguide which corresponds to the wall member of the reaction vessel is determined to be greater than w/tan θmin with respect to a thickness of the slab-type optical waveguide which corresponds to the lengthened portion, wherein a thickness of the wall member of the reaction vessel is determined to be w which wall member is formed between the slab-type optical waveguide which corresponds to the wall member of the reaction vessel and the slab-type optical waveguide which corresponds to the lengthened portion, a minimum value of a propagation angle within the slab-type optical waveguide is determined to be θmin.

As to the optical measurement apparatus according to claim 7, the apparatus is an apparatus in which a reaction vessel is formed by plural wall members one of which is a slab-type optical waveguide which totally reflects an exciting light, the slab-type optical waveguide is lengthened to exciting light incidenting side from the slab-type optical waveguide, and a thickness of the slab-type optical waveguide which corresponds to the wall member of the reaction vessel is determined to be greater than w/tan θmin with respect to a thickness of the slab-type optical waveguide which corresponds to the lengthened portion, wherein a thickness of the wall member of the reaction vessel is determined to be w which wall member is formed between the slab-type optical waveguide which corresponds to the wall member of the reaction vessel and the slab-type optical waveguide which corresponds to the lengthened portion, a minimum value of a propagation angle within the slab-type optical waveguide is determined to be θmin. Therefore, a disadvantage is securely prevented from occurence that a part of a light propagates within the wall member of the reaction vessel which is formed between the slab-type optical waveguide which corresponds to the wall member of the reaction vessel and the slab-type optical waveguide which corresponds to the lengthened portion which light propagates from the slab-type optical waveguide which corresponds to the lengthened portion to the slab-type optical waveguide which corresponds to the wall member of the reaction vessel. When it is supposed that the part of the light propagates within the wall member, it is not guaranteed that the part of the light propagates within the wall member in a total reflection manner, so that the light intrudes within the reaction vessel so as to possibly excite fluorescence dye within unreacted reagent which are floating within the reaction vessel. Further, when the part of the light propagates within the wall member in a total reflection manner, fluorescence dye existing in vicinity to the wall member (fluorescence dye which are apart from a surface of the slab-type optical waveguide) is excited. And, a part of fluorescent light from those fluorescence dye is mixed to fluorescent light which is a real signal light so that the part of fluorescent light becomes a noise and causes lowering in optical measurement sensitivity and accuracy. But, in the optical measurement apparatus according to claim 7, the part of the light is prevented from intruding into the wall member so that the above disadvantage is securely prevented from occurence and the optical measurement sensitivity and accuracy is improved.

An optical measurement apparatus according to claim 8 is an apparatus in which the detector is disposed in the exciting light incidenting side and is disposed so as to detect fluorescent light component which is outgone from a portion of the slab-type optical waveguide which portion is apart from an optical axis of the exciting light by a predetermined distance, and in which a total reflection prism is formed on the slab-type optical waveguide which total reflection prism guides the fluorescent light to the detector which fluorescent light propagates to the edge face of the slab-type optical waveguide.

As to the optical measurement apparatus according to claim 8, the detector is disposed in the exciting light incidenting side and is disposed so as to detect fluorescent light component which is outgone from the portion of the slab-type optical waveguide which portion is apart from the optical axis of the exciting light by the predetermined distance, and the total reflection prism is formed on the slab-type optical waveguide which total reflection prism guides the fluorescent light to the detector which fluorescent light propagates to the edge face. Therefore, outgoing direction of the fluorescent light is easily changed which fluorescent light is outgone from the slab-type optical waveguide. Consequently, a disposing position of an optical system for collecting fluorescent light is easily changed by forming the total reflection prism. And, the fluorescent light is outgone from the portion which is apart from the optical axis of the exciting light by the predetermined distance so that no optical element for separating the exciting light and the fluorescent light is required so as to simplify the arrangement of the optical system even when the fluorescent light is outgone in parallel to the optical axis of the exciting light, for example.

An optical measurement apparatus according to claim 9 is an apparatus in which the detector is disposed to detect fluorescent light component which is outgone from one side edge face of the slab-type optical waveguide, and in which a total reflection prism is formed on the other side edge face of the slab-type optical waveguide which prism guides fluorescent light to the one side edge face which fluorescent light propagates to the other side edge face.

As to the optical measurement apparatus according to claim 9, the detector is disposed to detect fluorescent light component which is outgone from one side edge face of the slab-type optical waveguide, and the total reflection prism is formed on the other side edge face of the slab-type optical waveguide which prism guides fluorescent light to the one side edge face which fluorescent light propagates to the other side edge face. Therefore, other fluorescent light component which is to be outgone in a reversed direction with respect to one fluorescent light component, is outgone in the same direction to that of the one fluorescent light component, so that fluorescent light components which are to be outgone in two directions, can be detected using only one optical system and one detector. Therefore, detectable fluorescent light component is increased without increasing a number of optical systems and detectors.

An optical measurement apparatus according to claim 10 is an apparatus in which plural total reflection prisms are formed.

As to the optical measurement apparatus according to claim 10, plural total reflection prisms are formed. Therefore, a propagating distance of fluorescent light by each total reflection prism is shortened. And, a quantity of the fluorescent light component which can be detected by a detector, is increased due to shortening of the propagating distance.

An optical measurement apparatus according to claim 11 is an apparatus in which a lens having an arc shaped outgoing face is formed on the edge face of the slab-type optical waveguide which lens collects fluorescent light component which is to be detected by the detector.

As to the optical measurement apparatus according to claim 11, the lens having the arc shaped outgoing face is formed on the edge face of the slab-type optical waveguide which lens collects fluorescent light component which is to be detected by the detector. Therefore, the fluorescent light component is collected to some degree by the lens so that load of a collecting lens is decreased which collecting lens is included within an outer optical system.

BEST MODES FOR UTILIZING THE INVENTION

Hereinafter, referring to the attached drawings which illustrate embodiments, we explain the present invention in detail.

Figure 1:
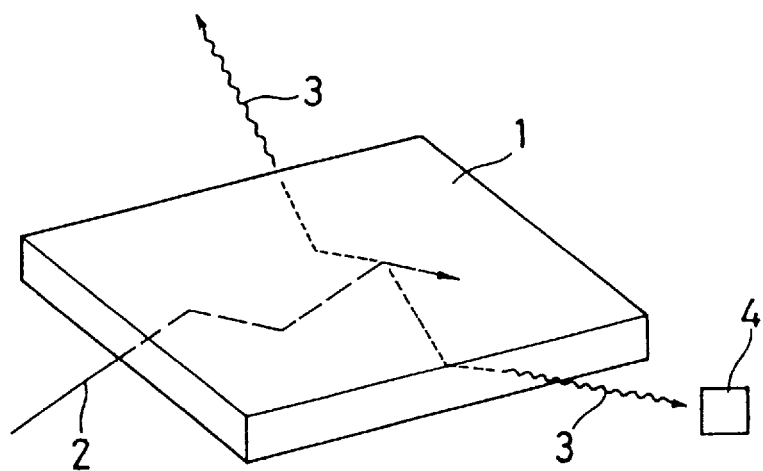
FIG. 1 is a perspective view schematically illustrating an embodiment of an optical measurement apparatus according to the present invention.
Figure 2:
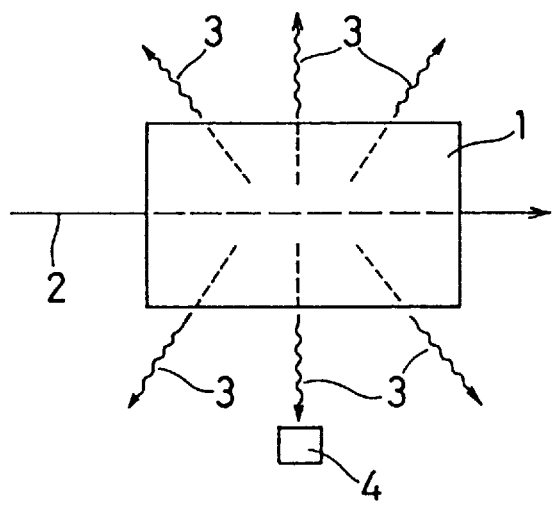
FIG. 2 is a plan view of the same.

FIG. 1 is a perspective view schematically illustrating an embodiment of an optical measurement apparatus according to the present invention, whicle FIG. 2 is a plan view of the same. When an exciting light 2 is introduced within a slab-type optical waveguide 1, fluorescent light propagates within the slab-type optical waveguide 1 isotropically which fluorescent light is excited by an evanescent which is caused by the exciting light 2, and a part of fluorescent light is received by a fluorescent light detector 4 which fluorescent light is radiated from the slab-type optical waveguide 1 in a direction which is different from an optical axis of the exciting light 2. Relative angles of a face for radiating the fluorescent light to exterior of the slab-type optical waveguide 1 with respect to an exciting light incidenting face, an exciting light outgoing face, and a face for totally reflecting the exciting light, are 45°–135°. It is preferable that the relative angles are 90° in real. In FIGS. 1 and 2, an optical system such as a light collecting lens and the like is omitted for simplification. Further, in FIGS. 1 and 2, an exciting light outgoing section such as a prism and the like (not shown) may be provided at an end edge section of an exciting light propagating path so that the exciting light 2 introduced within the slab-type optical waveguide 1 is prevented from being reflected at the end edge section of the exciting light propagating path and is prevented from propagating within the slab-type optical waveguide 1 again. It is also possible that paint for absorbing or decreasing the exciting light 2 at a predetermined extent of the slab-type optical waveguide 1 which extent includes the end edge section, or that a predetermined extent of the slab-type optical waveguide 1 which extent includes the end edge section, is faces to a vessel which houses a substance for absorbing or decreasing the exciting light 2, so that the exciting light 2 is absorbed or decreased and the exciting light outgoing section is omitted.

When the above arrangement is employed, the optical axis of the exciting light and an optical axis of fluorescent light is perfectly separated so that a disadvantage is prevented from occurence that an exciting light reflected or scattered by an optical element is detected by the fluorescent light detector 4. Of course, a scattered exciting light is prevented from being detected by the fluorescent light detector 4 which scattered exciting light is due to adhesion of dust, reagent and the like to optical elements (lens, filter, window and the like) which are included within an optical system. Further, no dichroic mirror is required which dichroic mirror separates the exciting light and the fluorescent light, and it is possible that a lens having a shorter focal distance is employed and the lens and the like are disposed in closed condition to the exciting light incidenting edge of the slab-type optical waveguide 1, so that the optical system is decreased in size and is simplified in its entirety. Furthermore, the optical axis of the exciting light and an optical axis of the optical system which collects fluorescent light and guides the collected fluorescent light to the fluorescent light detector 4, are not required to be coincident partially to one another so that freedom of disposition of the optical system is greatly raised. Further, freedom of disposition of the optical elements included within the optical system is greatly raised, countermeasure for soil of the optical elements is easily performed. Furthermore, an optical measurement signal is enlarged by increasing a number of detectors which detects fluorescent light. Further, it is possible that fluorescent light component is detected within a wider extent by lengthening the length of the slab-type optical waveguide in an exciting light propagating direction, so that an optical measurement signal is enlarged.

Figure 27:
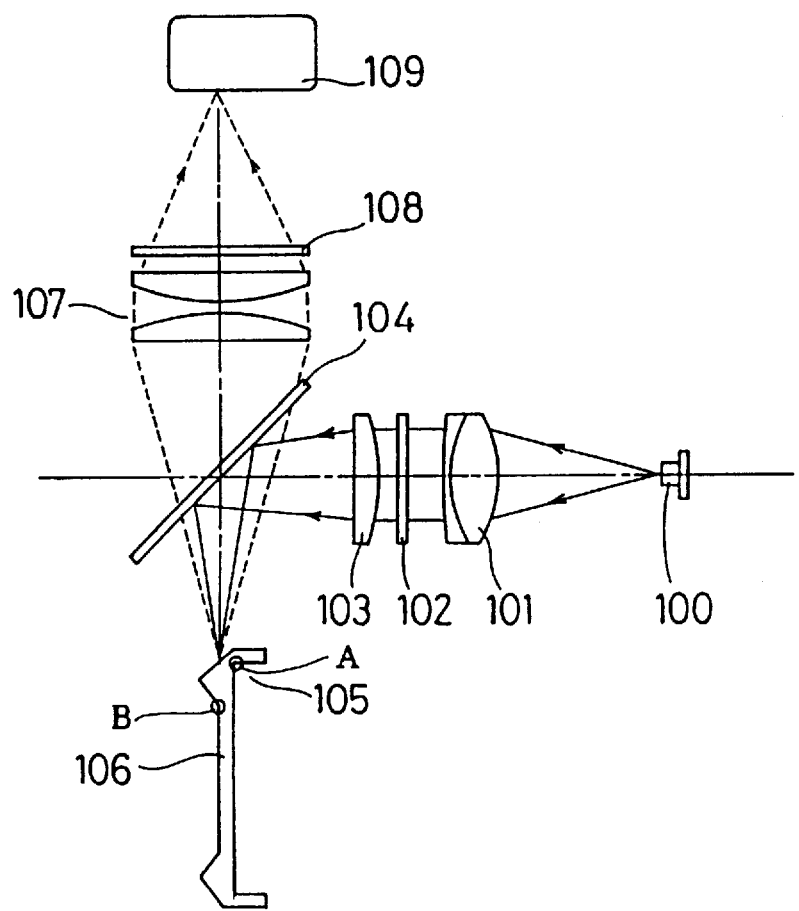
FIG. 27 is a diagram schematically illustrating a conventional apparatus.

When the conventional apparatus illustrated in FIG. 27 is employed, for example, it is general that an exciting light is focused to suit a cross sectional shape of a slab-type optical waveguide, and the exciting light is incident in this condition into the slab-type optical waveguide. This arrangement increases a focusing size of the exciting light in comparison to a case in which an exciting light is focused to be a point shape, therefore focusing is easily achieved, and an energy of an exciting light at the focusing point is lowered so that degradation of fluorescent substance due to the energy of the exciting light is softened. But, an exciting light irradiation system should be constituted using a cylindrical plane lens and a normal spherical lens, for example. As a result, increase in cost is realized due to employment of the cylindrical plane lens. Further, a relative relationship between a cylindrical axis of the cylindrical plane lens and a waveguiding direction of the slab-type optical waveguide 1 should be accurately determined, therefore working accuracy of a holder for holding lenses should be raised, and additional adjusting processing is required. On the contrary in this embodiment, limitation of degradation of fluorescent substance due to the exciting light is easily eliminated, in this turn the exciting light irradiation system is constituted using only spherical lenses, so that the optical system is simplified and is decreased in cost.

Figure 3:
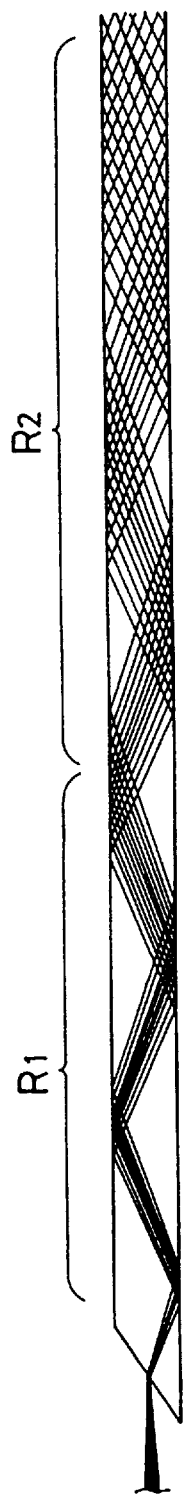
FIG. 3 is a schamatic side view of a slab-type optical waveguide illustrating variation in energy density.
Figure 25:
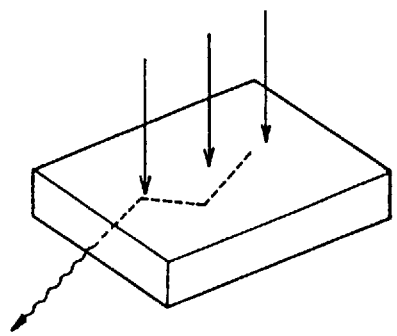
FIG. 25 is a perspective view useful in understanding a principle of a conventional method.
Figure 26:
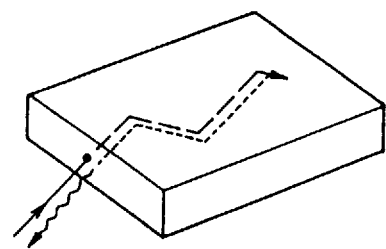
FIG. 26 is a perspective view useful in understanding a principle of a conventional method.

Further, when the conventional method illustrated in FIG. 25 is employed, entire region on an optical axis on which an exciting light propagates within a slab-type optical waveguide, is included within a viewfield of a fluorescent light detector. But in this embodiment, the optical axis of the exciting light and the optical axis of the fluorescent light are shifted by the predetermined angle (preferably shifted by 90°) from one another so that only a voluntary region among the above entire region can be positioned within the viewfield of the fluorescent light detector. Therefore, a neighbouring portion of the exciting light incidenting edge (refer to a region R1 in FIG. 3) is screened from the viewfield of the fluorescent light detector 4 which neighbouring portion has a higher energy density due to incdenting the exciting light into the slab-type optical waveguide 1 in a focused condition. And, only a region (refer to a region R2 in FIG. 3) which is apart from the exciting light incidenting edge and has lower energy density and is little possible of degrading of the fluorescent substance, is determined to be a measurable region.

Figure 4:
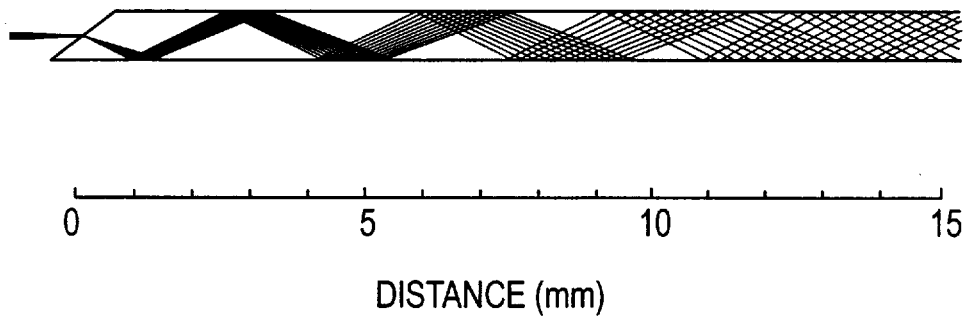
FIG. 4 is a side view of the slab-type optical waveguide schematically illustrating propagation of an exciting light.
Figure 5:
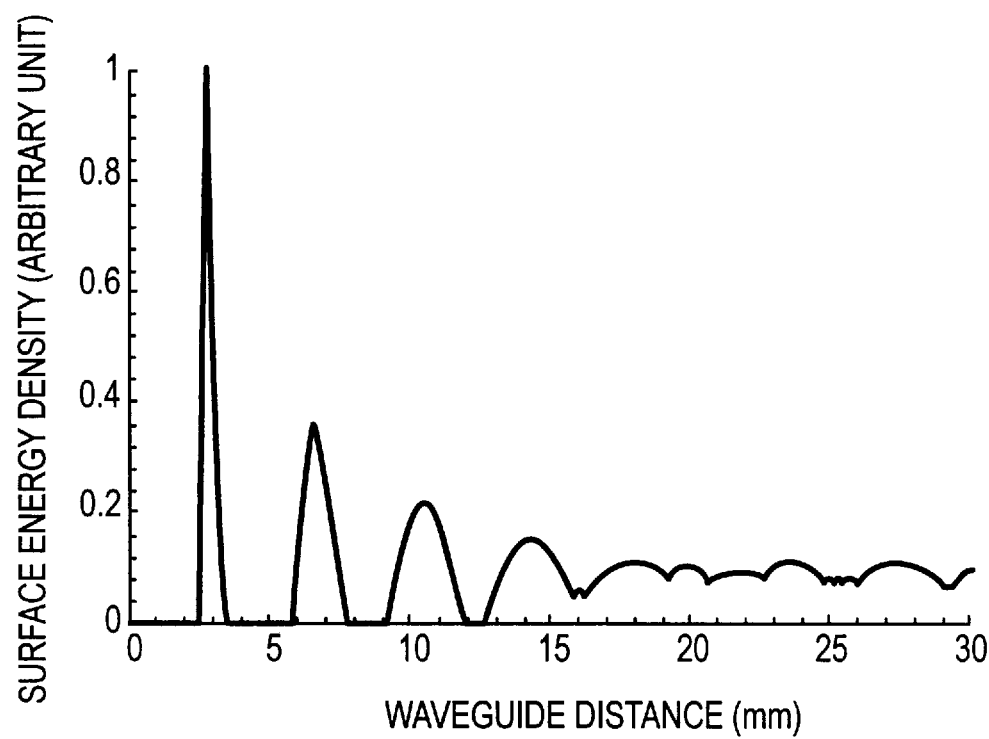
FIG. 5 is a graph illustrating a distribution of intensity of exciting light on a surface of the slab-type optical waveguide.

FIG. 4 is a diagram illustrating a simulation result of an exciting light which propagates within the slab-type optical waveguide, while FIG. 5 is a diagram illustrating a simulation result of intensity distribution of the exciting light on a surface of the slab-type optical waveguide 1. In the simulation, a slab-type optical waveguide 1 made of polymethyl methacrylate (refractive index is 1.491) is employed, and an apex angle is determined to be 35°. And, a thickness of the slab-type optical waveguide 1 is determined to be 0.75 mm, a numerical aperture of the lens (plane-convex spherical, plane-convex cylindrical plane lens doublet) of the exciting light irradiation system is determined to be F5.6, an image-formation prism is determined to be a wedge shaped leftmost edge of the slab-type optical waveguide illustrated in FIG. 4, a position of focal point is determined to be the center of the slope of the wedge shaped edge, a central value of propagation angles of the exciting light is determined to be 68.17°, and an extent of the propagation angles of the exciting light is determined to be 63.12°–72.30°. A luminous energy of the exciting light is arbitrarily determined.

As is apparent from FIG. 5, only a region in which almost uniform surface energy density due to the exciting light is obtained, is positioned within the viewfield of the fluorescent light detector 4 by screening a region by 0–15 mm from the exciting light incidenting edge of the slab-type optical waveguide 1.

Above values are optimum values of the specific example. It is preferable that optimum values are determined to every optical measurement apparatus by taking a numerical aperture of the exciting light irradiation system, a thickness of the slab-type optical waveguide, a luminous energy of exciting light, endurance of fluorescent substance against light quantity and the like, into consideration. As a result, a luminous energy of an exciting light is increased so that measurement sensitivity and measurement accuracy is improved when a laser is employed as the exciting light. Countermeasure is easily realized such that a margin of alignment between an optical axis of the exciting light and the slab-type optical waveguide 1 is increased by focusing the exciting light sufficiently at an incidenting spot. In other word, an alignment of the optical axis of the exciting light and the slab-type optical waveguide should be determined so as not to irradiate the exciting light to the edge of the exciting light incidenting face, in order to prevent leakage and propagating by an angle which is different from a designed angle of the exciting light from occurence, when the exciting light is incident in the exciting light incidenting face of the slab-type optical waveguide 1. An extent in which the alignment is determined to the above determination, is enlarged by incidenting the exciting light in the exciting light incidenting face under a condition that the exciting light is narrowed by sufficient focusing of the exciting light. Further, in a region of the optical waveguide which region is sufficiently apart from the exciting light incidenting face, reflecting spots at a surface of the optical waveguide overlap to one another and uniform irradiation is realized so that influence is lightened which is due to partial nonuniformity of reagent such as antibodies, antigens and the like which are fixed to a surface of the slab-type optical waveguide, which influence is also due to defect such as local disfigurement on the surface of the optical waveguide. When local disfigurement exists on the surface of the slab-type optical waveguide, a degree of influence (intensity of scattered exciting light and the like) due to the disfigurement varies depending upon intensity of a light which incidents in corresponding portion. And, a great influence is realized when disfigurement exists within a portion at which a light having a great intensity is irradiated. Further, within a predetermined extent of the slab-type optical waveguide which extent includes a portion at which a light having a great intensity is irradiated, an intensity of a light greatly varies even when a position of the slab-type optical waveguide slightly varies. Therefore, when a measurement value at an initial stage of fluorescence immunity reaction and a measurement value after the fluorescence immunity reaction has reached an equilibrium condition are measured and a difference between both measurement values is calculated, for example, slight positioning error is generated and influence of disfigurement for carrying out each measurement vary independently even when the slab-type optical waveguide 1 is positioned for each measurement. But in this embodiment, the uniform irradiation is realized as is described earlier, influence of disfigurement for carrying out each measurement become nearly equal to one another and consequently influence due to disfigurement is lightened, even when slight positioning error is generated as is described earlier.

SECOND EMBODIMENT

Figure 6:
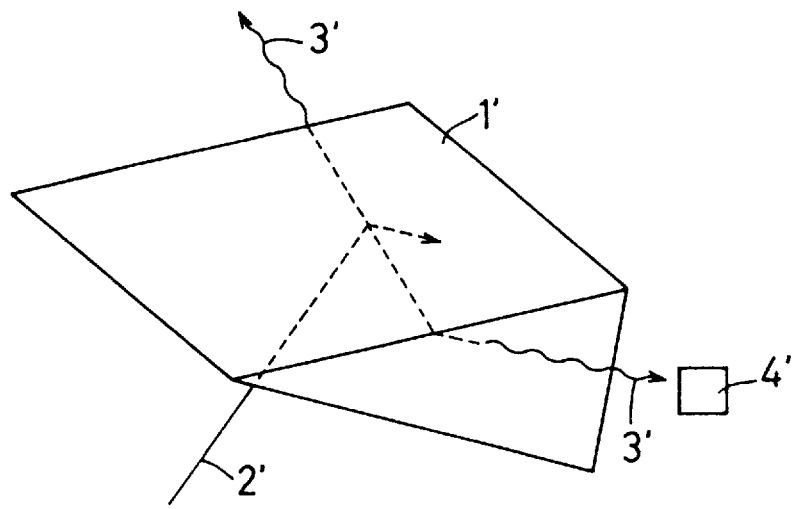
FIG. 6 is a perspective view of another embodiment of an optical measurement apparatus according to the present invention.
Figure 7:
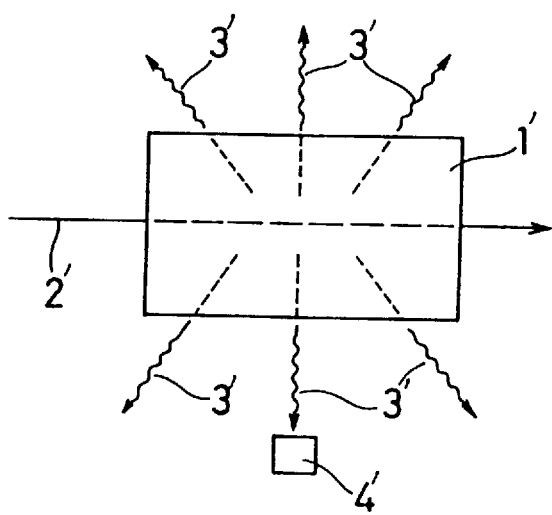
FIG. 7 is a plan view of the same.

FIG. 6 is a perspective view schematically illustrating an optical measurement apparatus of another embodiment according to the present invention, whice FIG. 7 is a plan view of the same. This embodiment differs from the above embodiment in that a totally reflecting prism 1' is employed instead of the slab-type optical waveguide 1.

In this embodiment, an exciting light 2' is introduced from a incidenting face of the totally reflecting prism 1', the introduced exciting light 2' is totally reflected and is outgone thereafter. During this operation, fluorescent light 3' propagates within the totally reflecting prism 1' in every direction which fluorescent light 3' is excited by an evanescent wave which is due to the totally reflected exciting light 2', and a part of fluorescent light is received by a fluorescent light detector 4' which fluorescent light is outgone from the totally reflecting prism 1' in a direction which is different from an optical axis of the exciting light 2'.

Therefore, this embodiment prevents a disadvantage from occurence that a light which is reflected by an optical element or is scattered by an optical element is also detected by the fluorescent light detector 4', because the optical axis of the exciting light and an optical axis of the fluorescent light is perfencly separated from one another. Of course, a disadvantage is prevented from occurence that a scattered exciting light due to adhesion of dust, reagent and the like to optical elements (lens, filter and the like) included within an optical system, is detected by the fluorescent light detector 4'. Further, no dichroic mirror is required which dichroic mirror separates the exciting light and the fluorescent light, and it is possible that a lens having a shorter focal distance is employed and the lens and the like are disposed in closed condition to the exciting light incidenting edge of the slab-type optical waveguide 1, so that the optical system is decreased in size and is simplified in its entirety. Furthermore, the optical axis of the exciting light and an optical axis of the optical system which collects fluorescent light and guides the collected fluorescent light to the fluorescent light detector 4, are not required to be coincident partially to one another so that freedom of disposition of the optical system is greatly raised. Further, freedom of disposition of the optical elements included within the optical system is greatly raised, countermeasure for soil of the optical elements is easily performed. Furthermore, an optical measurement signal is enlarged by increasing a number of detectors which detects fluorescent light.

THIRD EMBODIMENT

Figure 8:
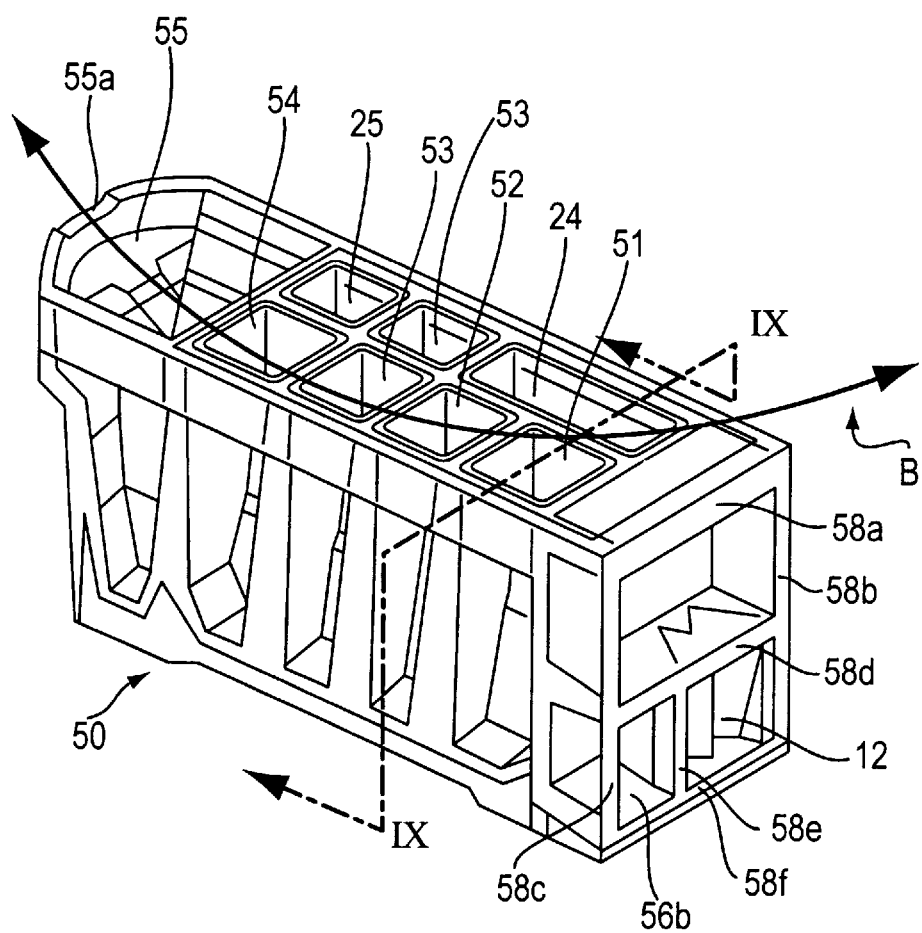
FIG. 8 is a perspective view of a further embodiment of an optical measurement apparatus according to the present invention.
Figure 9:
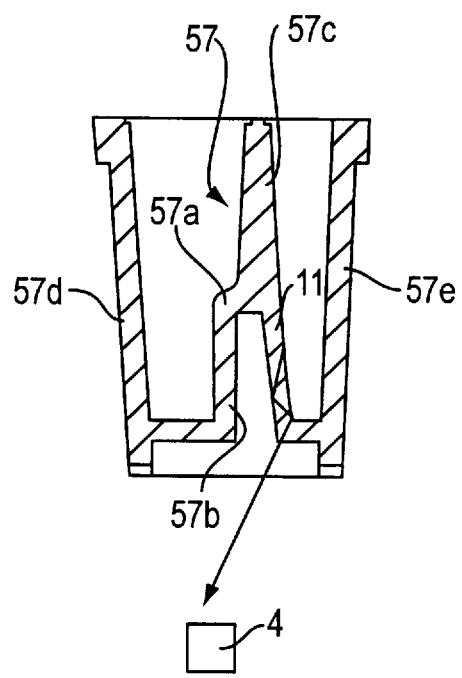
FIG. 9 is a cross sectional view taken along a line IX—IX in FIG. 8.
Figure 10:
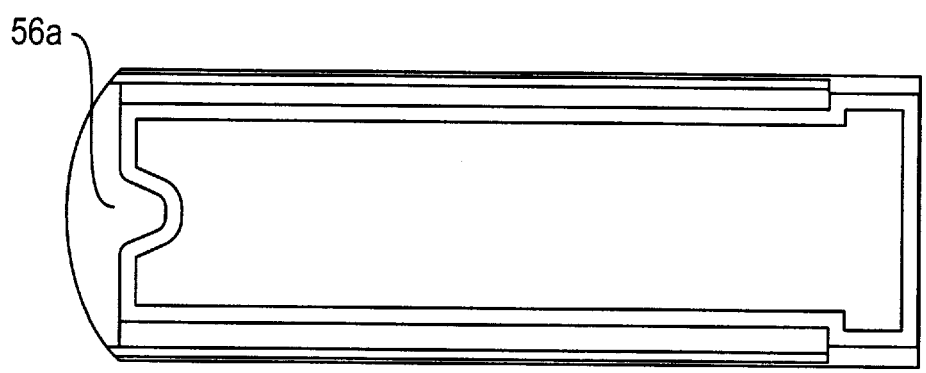
FIG. 10 is a bottom view of the optical measurement apparatus which is illustrated in FIG. 8.

FIG. 8 is a perspective view of an optical measurement apparatus of a further embodiment according to the present invention, FIG. 9 is a cross sectional view taken along a line IX—IX in FIG. 8, while FIG. 10 is a bottom view of the same. The optical measurement apparatus to its entirety is made of material which has transparency. In FIG. 10, display of an inner arrangement is omitted.

In the optical measurement apparatus, a dilution liquid vessel 51, a stirring vessel 52, a multi-function vessel 53 and a labeling liquid vessel 54 are disposed within a predetermined position of a casing 50 in this order in a longitudinal direction. Also, a reaction vessel 24, a multi-function vessel 53 and a light absorbant housing vessel 25 are disposed in this order within the casing 50 in a longitudinal direction. Disposition of the reaction vessel 24, the multi-function vessel 53 and the light absorbant housing vessel 25 is in parallel to the disposition of the dilution liquid vessel 51, the stirring vessel 52, the multi-function vessel 53 and the labeling liquid vessel 54. And, a test body vessel 55 is disposed in a opposed position to the labeling liquid vessel 54 and the light absorbant housing vessel 25. Also, the dilution liquid vessel 51, stirring vessel 52 and the multi-function vessel 53 are opposed to the reaction vessel 24, and the labeling liquid vessel 54 is opposed to the light absorbant housing vessel 25. Further, the reaction vessel 24, multi-function vessel 53 and light absorbant housing vessel 25 have side walls which are positioned toward the dilution liquid vessel 51, stirring vessel 52, multi-function vessel 53 and labeling liquid vessel 54, and the lower half of the side walls are made to be an optical waveguide body 11. And, a fluorescent light detector 4 such as a photomultiplier and the like is disposed beneath the optical waveguide body 11. Reference numeral 12 indicates a prism for introducing an exciting light into the optical waveguide body 11. Further, an optical system including a light collecting lens and the like is omitted in FIGS. 8–10.

More specifically, the dilution liquid vessel 51 is a vessel in which a liquid (dilution liquid) for diluting a test liquid is previously housed therein. The stirring vessel 52 is a vessel in which the test liquid and the dilution liquid are poured and both liquid are stirred by repeating sucking and discharging of both liquid by a required number of times using a nozzle (not shown). The multi-function vessel 53 is a vessel which is used for raising dilution, or is used for housing a reagent which raises an optical measurement sensitivity. More specifically, when dilution is raised, a diluted test liquid is poured in the multi-function vessel 53 from the stirring vessel 52 using a nozzle (not shown), also a dilution liquid is poured in the multi-function vessel 53, then sucking and discharging of a mixed liquid are repeated by a required number of times. When the multi-function vessel 53 is used for the latter object, a liquid including, for example, biotin-labeled-antibodies which are made by labeling antibodies with biotin, is previously housed therein. The labeling liquid vessel 54 is a vessel for housing a liquid including fluorescent-body-labeled-antibodies which are made by labeling antibodies with labeling fluorescent body, or fluorescent-body-labeled-avidin which are made by labeling avidin with labeling fluorescent body. The labeling liquid vessel 54 is not opposed to any one of side walls of the reaction vessel 24, so that a condition is maintained that the reaction vessel 24 is scarcely influenced by a fluorescent light which fluorescent light is radiated from the labeling fluorescent body which is excited by an exciting light propagating within the optical waveguide 11. The test body vessel 55 is a vessel in which a test liquid such as blood and the like is temporarily housed. A sealing member (not shown) made of aluminium and the like is provided to cover all vessels excepting the test body vessel 55. Further, the test body vessel 55 has a concave portion 55a for pouring test liquid at a predetermined position at an upper edge of the side wall, and a lower portion of the test liquid vessel 55 is formed so as to have a narrow width so that the test liquid vessel 55 is opposed to only the labeling liquid vessel 54. Further, an engaging concave portion 56a which elongates up and down in correspondence to the concave portion 55a, is formed and an engaging concave portion 56b is formed at a predetermined position which position is neighhbouring to the prism 12 so that a positioning of the prism 12 with respect to an optical axis of an optical system is realized by engaging both engaging concave portions 56a and 56b with chucks (not shown), for example.

Further, The dilution liquid vessel 51, stirring vessel 52, multi-function vessel 53 and labeling liquid vessel 54 employs an inclined wall 57 which has a steped section 57a at its mid-height portion, as a side wall which exists in the reaction vessel 24 ward side. an inclined wall 57b which exists downward from the stepped section 57a, is opposite to the optical waveguide 11 and a little clearance exists therebetween, and an inclined wall 57c which exists upward from the stepped section 57a, is united to the side wall of the reaction vessel 24. Further, an inclined wall 57d which has an inclination which is reverse to the inclination of the inclined wall 57, is employed as a side wall which is opposite to the inclined wall 57. Of course, an inclined wall 57e which has an inclination which is reverse to the inclination of the optical waveguide 11, is employed as a side wall which is one of side walls of the reaction vessel 24 and is opposite to the inclined wall 57c. And, thicknesses of the stepped section 57a and all inclined walls 57b, 57c, 57d and 57e are determined to be equal to a thickness of a bottom plate of the casing 50 so that deformation which occurs during formation is greatly decreased. Further, the inclined walls 57b, 57c, 57d and 57e are inclined by 3° with respect to a vertical plane, and a surface of the optical waveguide 11 which is obtained by the formation is made to be a mirror face. Furthermore, thicknesses of assistance plates 58a, 58b, 58c, 58d, 58e and 58f which elongate horizontally from a face on which the prism 12 was formed, are determined to be equal to one another, so that deformation which occurs during formation is greatly decreased and the prism 12 is prevented from being touched by a hand, finger and the like. Further, a number of vessels which are formed in the optical measurement apparatus is great so that a number of side walls each of which partitions neighbouring vessels is inevitably great. Consequently, strength of the optical measurement apparatus in its entirety is improved. Further, in FIG. 9, very small stepped sections which are formed at opening edge portions, are used for securing the sealing with the sealing member.

Further, a locus B of a nozzle as is illustrated in FIG. 8, is determined to pass through above positions with respect to the reaction vessel 24, stirring vessel 52, multi-function vessel 53, labeling liquid vessel 54 and test body vessel, so that movement of the nozzle which is required for optical measurement is sufficiently along to the locus B. The nozzle should be moved to the above position with respect to the dilution liquid vessel 51, but this movement is sufficiently carried out relatively earlier stage of the optical measurement so that the nozzle is moved out from the locus B.

When normal fluorescent immuno assay is carried out using the optical measurement apparatus having the above arrangement, an optical measurement apparatus of which labeling liquid vessel 54 fluorescent body labeled antibodies are previously housed therein, is employed.

At first, the sealing member is peeled from the optical measurement apparatus, then an edge portion of an opening of a test tube (not shown) is engaged to the concave portion 55a, thereafter the test tube is inclined so that a test liquid such as blood and the like is poured to the test body vessel 55. Then, the optical measurement apparatus is positioned by engaging the engaging concave portions 56A and 56b to the chuck claew (not shown). Thereafter, the nozzle (not shown) is moved to the above positions with respect to the stirring vessel 52 and the test body vessel 55. The nozzle is moved downward so as to suck a dilution liquid, test liquid, respectively. The nozzle is moved upward, and is then moved to the above position of the stirring vessel 53. The nozzle is moved downward so as to discharge the dilution liquid and test liquid. In this condition, sucking and duscharging by the nozzle are repeated by a required number of times so that stirring of the dilution liquid and the test liquid is carried out.

After the above pre-operation has been finished, the diluted test liquid within the stirring vessel 53 is sucked by the nozzle. The nozzle is moved upward, is moved to the above position with respect to the reaction vessel 24, and is moved downward so that the diluted test liquid is discharged therefrom. Therefore, antigen-antibody reaction is carried out between antibodies which are previously fixed to the optical waveguide body 11 and antigens included within the test liquid. After the antigen-antibody reaction has carried out foe a predetermined time period, all test liquid within the reaction vessel 24 is sucked by the nozzle. The nozzle is moved upward and is moved to a disposal section (not shown) so that the test liquid is discharged. In this case, cleaning of the nozzle is carried out when it is required. Then, the nozzle is moved to the above position with respect to the labeling liquid vessel 54, and is moved downward so that a liquid including fluorescent-body-labeled-antibodies is sucked therein. The nozzle is then moved upward, is moved to the above position with respect to the reaction vessel 24, and is moved downward so that the liquid including fluorescent-body-labeled-antibodies is discharged therefrom. Therefore, antigen-antibody reaction is carried out between antigens which are bound in vicinity of the surface of the optical waveguide body 11 by the above antigen-antibody reaction, and the fluorescent-body-labeled-antibodies. The fluorescent-body-labeled-antibodies are bound in vicinity of the surface of the optical waveguide body 11 by this antigen-antibody reaction, so that labeling fluorescent body of the bound fluorescent-body-labeled-antibodies are excited by the evanescent wave component, and the labeling fluorescent body radiates characteristic fluorescent light. Of course, the exciting light introduced within the optical waveguide body 11 through the prism 12 is guided finally to the light absorbant housing vessel 25 so that scarce exciting light component returns to the prism 12. Also, influence due to fluorescent light which is possibly radiated from the labeling liquid vessel 54 becomes scarce. Consequently, a degree of immunity reaction is accurately measured based upon the characteristic fluorescent light. Wherein, only fluorescent light which intrudes to the optical waveguide body 11, propagates downward within the optical waveguide body 11 in a total reflection manner, and is outgone downward from the optical waveguide body 11, among the characteristic fluorescent light is detected by the fluorescent light detector 4. Therefore, fluorescent light scarcely influenced by reflected light and the like of the exciting light is detected so that the optical measurement accuracy is improved. Further, an optical measurement which is not influenced by degradation of fluorescent substance is achieved by screening a region which is neighbouring to the prism 12 (a region in which an energy density of the exciting light is high), from the fluorescent light detector 4. When the screening position and screening extent are varied, luminous energy of fluorescent light for detection varies. But, the variation of luminous energy of fluorescent light for detection is in proportion to a rate of variation in screening position with respect to a length of a region of the optical waveguide body 11 which region is not screened, therefore positioning accuracy which is required for screening can be comparatively roughly determined. Specifically, when a width of a non-screened region is 10 mm and an optical measurement with an accuracy of 1% is to be carried out, reproducable accuracy of the width should be determined to equal to or less than ±0.1 mm which accuracy is easily realized. Also, a position of a detection region influences the measurement. But, the apparatus determineds a region in which ununiform irradiation due to the exciting light is small, of the optical waveguide body 11 as a detection region so that influence due to the position of the detection region is fairly decreased. Therefore, the screening is achieved by applying a screening function to the casing 20 itself by employing a screening plate, paint, prism and the like. Also, the screening is achieved by determining a desired opening, diaphragm to a fluorescent light detecting optical system which guides fluorescent light to the fluorescent light detector 4.

When hepatitis marker, cancer marker and the like is measured using the optical measurement apparatus having the above arrangement, the optical measurement apparatus is used in which a liquid including biotin labeled antibodies is previously housed within the labeling liquid vessel 54, and a liquid including fluorescent-body-labeled-avidin is housed within the multi-function vessed 53.

In this case, antigen-antibody reaction is carried out between antigens included within the test liquid and antibodies previously fixed to the optical waveguide body 11. Then, the test liquid is disposed. Thereafter, the nozzle is moved to the above position with respect to the multi-function vessel 53, is moved downward so as to suck the liquid including biotin labeled antibodies, and is moved upward. The nozzle is then moved to the above position with respect to the reaction vessel 24, and is moved downward so as to discharge the liquid including biotin labeled antibodies. Therefore, antigen-antibody reaction is carried out between the antigens which are bound in vicinity of the surface of the optical waveguide body 11 by the above antigen-antibody reaction and the biotin labeled antibodies. Then the liquid including the biotin labeled antibodies is sucked and is disposed in similar way to that of the test liquid. Thereafter, the nozzle is moved to the above position with respect to the labeling liquid vessel 54, and is moved downward so as to such the liquid including fluorescent-body-labeled-avidin. The nozzle is then moved upward, is moved to the above position with respect to the reaction vessel 24, and is moved downward so as to discharge the liquid including fluorescent-body-labeled-avidin. Therefore, biotin which are bound in vicinity of the surface of the optical waveguide 11 by the above antigen-antibody reaction and the fluorescent-body-labeled-avidin are bonded to one another. The fluorescent-body-labeled-avidin are bound in vicinity of the surface of the optical waveguide 11 by the bonding, so that the labeling fluorescent body of the bound fluorescent-body-labeled-avidin is excited by the evanescent wave component and the labeling fluorescent body radiates characteristic fluorescent light. A quantity of labeling fluorescent bodies which are bound in vicinity of the surface of the optical waveguide body 11 by the bonding of biotin and avidin, is greater than a quantity of labeling fluorescent bodies which are bound by fluorescent-body-labeled-antibodies by several times (5-10 times), so that the bound labeling fluorescent bodies radiate fluorescent light which has sufficient luminous energy. Therefore, the optical measurement is performed based upon the fluorescent light.

FOURTH EMBODIMENT

Figure 11:
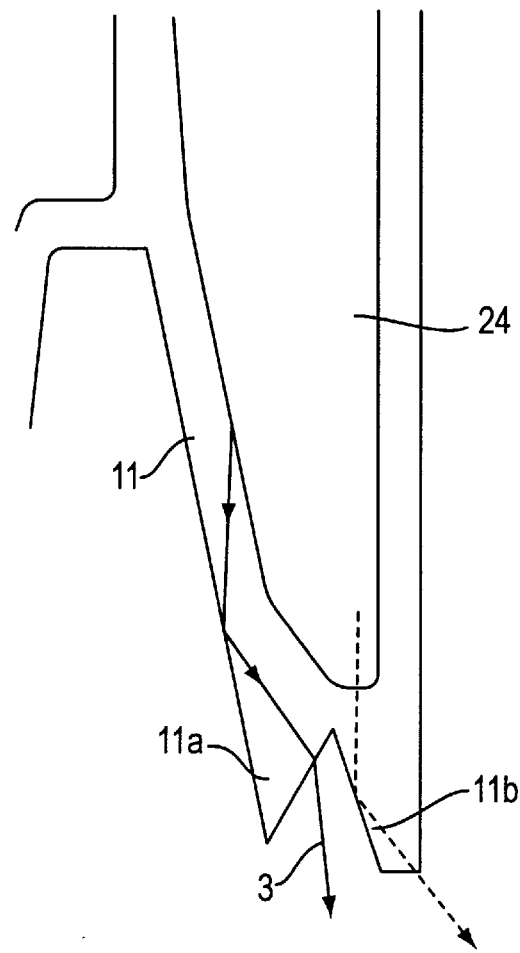
FIG. 11 is a cross sectional view of a main portion of yet another embodiment of an optical measurement apparatus according to the present invention.

FIG. 11 is a cross sectional view of a main portion of an optical measurement apparatus of yet another embodiment according to the present invention. The optical measurement apparatus differs from the embodiment in FIG. 9 in that a prism 11a is further provided at a fluorescent light outgoing section which is at the bottom edge of the optical waveguide body 11, and that an assistance prism 11b is further provided neighbouring to the prism 11a.

The prism 11a efficiently outgoes fluorescent light therefrom which fluorescent light is near a critical angle θc {θc=sin$^{-1}$ (n2/n1), wherein n1 represents a refractive index of the optical waveguide, while n2 represents a refractive index of a liquid within the reaction vessel 24}. And, the assistance prism 11b prevents the reaction vessel 24 from being entered within the viewfield of the fluorescent light detector 4. That is, a fluorescent light as a signal light is effectively collected by providing the prism 11a because it is known that fluorescent light propagating within the optical waveguide body 11 has maximum luminous energy at an angle which is near the critical angle θc. Further, the assistance prism 11b guides fluorescent light (stray light) which is possibly generated at a position which is within the reaction vessel 24 and which position is apart from the optical waveguide body 11, to out of the viewfield of the fluorescent light detector (not shown). The assistance prism 11b acts as a stray light screening member for the fluorescent light detector. A dashed line in FIG. 11 represents the stray light.

FIFTH EMBODIMENT

Figure 12:
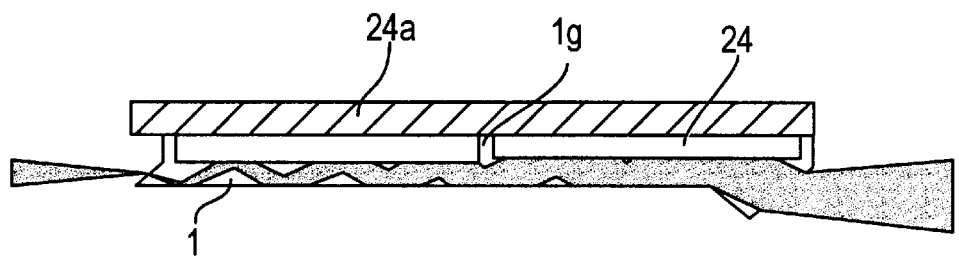
FIG. 12 is a cross sectional view schematically illustrating a yet further embodiment of an optical measurement apparatus according to the present invention.
Figure 13:
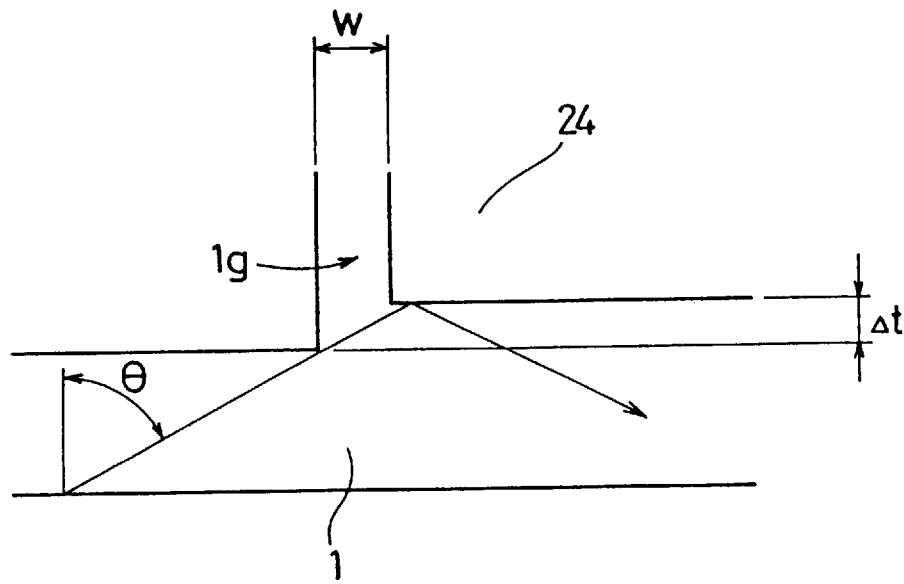
FIG. 13 is a side view useful in understanding a relationship between a width of a partitioning wall member and a difference in level of a slab-type optical waveguide.

FIG. 12 is cross sectional view schematically illustrating a main portion of an optical measurement apparatus of a yet further embodiment according to the present invention, while FIG. 13 is an enlarged cross sectional view illustrating a main portion of FIG. 12. A partitioning wall member 1g is formed in one body to the slab-type optical waveguide 1 so that the reaction vessel 24 is formed only at a region in which almost uniform surface energy density due to the exciting light is obtained. A member 24a for forming the reaction vessel 24 may be manufactured in separate body from the partitioning wall member 1g and is made in one body by adhesive agent and the like thereafter. And, a thickness of the slab-type optical waveguide 1 in exciting light incidenting side with respect to the partitioning wall member 1g is determined to be smaller than that of the slab-type optical waveguide 1 in other portion (refer to FIG. 13). When a difference Δt between the thicknesses of the slab-type optical waveguide 1 is determined to satisfy a relationship of Δt>w/tan θmin so that a disadvantage is prevented from occurence that the exciting light 2 intrudes into the partitioning wall member 1g, wherein a width of the partitioning wall member 1g is supposed to be w, and a minimum value of angles of the exciting light 2 is supposed to be θmin. When the exciting light 2 intrudes into the partitioning wall member 1g, it is not guaranteed that the exciting light propagates in a total reflection manner within the partitioning wall member 1g so that the exciting light may intrude into the reaction vessel 24 so as to excite fluorescence dye which is floating within the reaction vessel 24. Further, when the exciting light propagates in a total reflection manner within the partitioning wall member 1g, evanescent wave component may excite fluorescence dye which is apart from the surface of the slab-type optical waveguide 1 and exists in vicinity of the partitioning wall member 1g. And, fluorescent light radiated by those excited fluorescence dye becomes a noise source. But in this embodiment, the exciting light 2 is securely prevented from intruding into the partitioning wall member 1g, as is described earlier, so that generation of the noise source is prevented from occurence. Further, a stepped section due to the formation of the partitioning wall member 1g never influences badly to fluorescent light which propagates in a propagating direction which is different from a propagating direction of the exciting light (for example, a propagating direction which crosses by a nearly right angle with a propagating direction of the exciting light).

SIXTH EMBODIMENT

Figure 14:
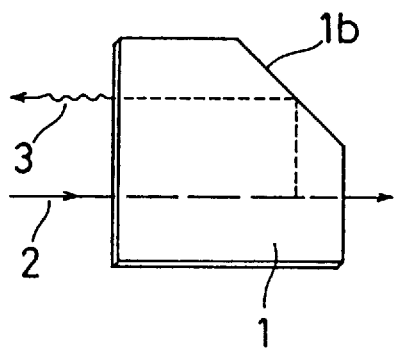
FIG. 14 is a perspective view schematically illustrating a main portion of still another embodiment of an optical measurement apparatus according to the present invention.

FIG. 14 is a perspective view of a main portion of an optical waveguide of still another embodiment according to the present invention. This embodiment differs from the embodiment in FIG. 12 in that a total reflection prism 1b is formed in the slab-type optical waveguide 1 at an end edge side in the propagating direction of the exciting light and at an edge section in a direction which crosses by a nearly right angle with an optical axis of the exciting light. Further, a formed position of the total reflection prism 1b is determined so that an optical axis of fluorescent light which is reflected by the total reflection prism 1b, is apart from the optical axis of the exciting light by more than a predetermined distance.

Therefore, in this embodiment, fluorescent light 3 which propagates within the slab-type optical waveguide 1 in a direction which crosses by a nearly right angle with a propagating direction of the exciting light 2, is reflected by the total reflection prism 1b so that the fluorescent light 3 propagates in a direction which is reverse to the propagating direction of the exciting light 2. That is, a reflection face of the total reflection prism faces air so that a critical angle for total reflection becomes a value which is near 40°. Therefore, the optical axis of the fluorescent light is is transformed to an optical axis which is at right angle with respect to the former optical axis. The transformed optical axis of the fluorescent light is apart from the optical axis of the exciting light by more than the predetermined distance so that no optical elements for separating the fluorescent light and the exciting light is required and an arrangement of an optical system is simplified.

When this arrangement is employed, incidenting of the exciting light and outgoing of the fluorescent light are achieved at the same side to one another of the slab-type optical waveguide 1 so that limitation for system layout is lightened. That is, when an optical measurement (fluorescent immuno assay and the like) is carried out using a casing in which a slab-type optical waveguide is installed, and even when mechanisms for achieving various operation are disposed in a neighbouring portion to the casing due to a demand for simultaneously carrying out incidenting and outgoing of light, and various operation such as operation of reaction liquid and the like, interference of the mechanisms with the optical system is securely avoided.

SEVENTH EMBODIMENT

Figure 15:
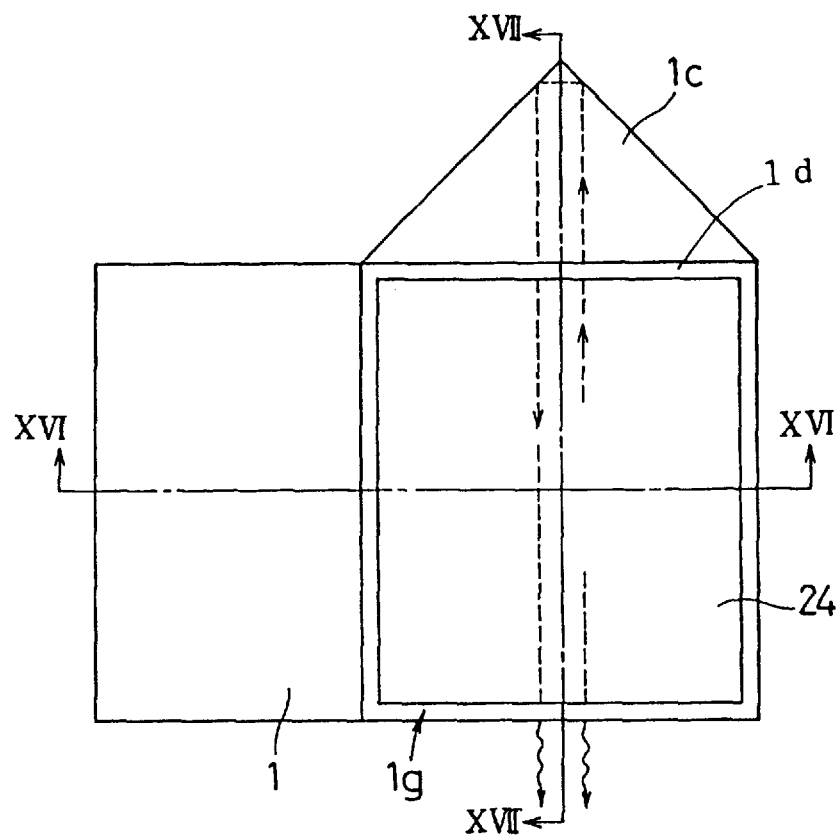
FIG. 15 is a still further embodiment of an optical measurement apparatus according to the present invention.
Figure 16:
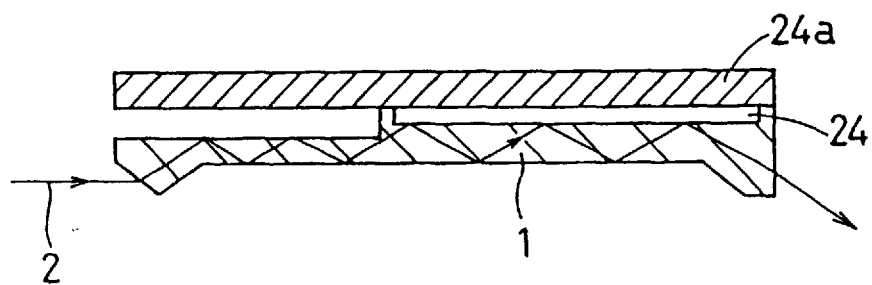
FIG. 16 is a cross sectional view taken along a line XVI—XVI in FIG. 15.
Figure 17:
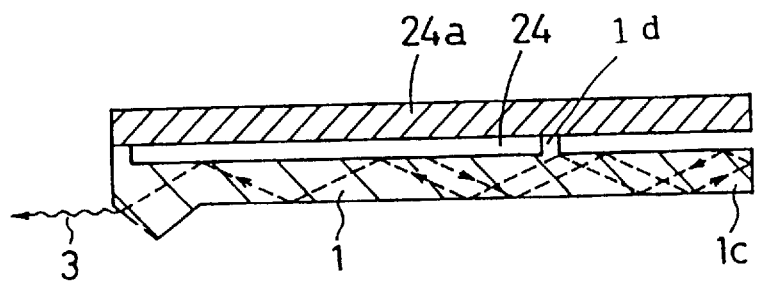
FIG. 17 is a cross sectional view taken along a line XVII—XVII in FIG. 15.

FIG. 15 is a plan view schematically illustrating an optical measurement apparatus of a still further embodiment according to the present invention, FIG. 16 is a cross sectional view taken along a line XVI—XVI in FIG. 15, and FIG. 17 is a cross sectional view taken along a line XVII—XVII in FIG. 15. This embodiment differs from the embodiment illustrated in FIG. 12 in that a rectangular total reflection prism 1c is provided on one side of the slab-type optical waveguide 1, which side is a side in a direction which crosses the optical axis of the exciting light by a right angle.

Therefore, in this embodiment, one of fluorescent lights which are to be outgone in two directions which cross the optical axis of the exciting light by a right angle, is reflected by the rectangular total reflection prism 1c, so that the reflected fluorescent light propagates within the slab-type optical waveguide 1 in a reversed direction and then outgoes from the slab-type optical waveguide 1 in a direction which is the same to that of the other fluorescent light. The fluorescent lights which are to be outgone in two directions, are detected by employing only one fluorescent light collecting optical system and one fluorescent light detector 4 so that sensitivity and accuracy in optical measurement are improved. Further, when the fluorescent lights which are to be outgone in two directions, are detected simply, two fluorescent light collecting optical systems and one fluorescent light detectors are needed. Therefore, the arrangement of the optical measurement apparatus is greatly simplified by employing this embodiment. Consequently, limitation for system layout is lightened.

Further, fluorescent light crosses the partitioning wall member 1d and propagates bidirectionally within a region of the slab-type optical waveguide 1 which region is positioned toward the rectangular total reflection prism 1c. Therefore, it is not preferable that a stepping difference (a difference of thicknesses) is provided to the slab-type optical waveguide i within this optical path. But, scattering of fluorescent light causes only lowering of a luminous energy for detection in comparison to that scattering of exciting light causes a great noise, so that the former is permitted when the lowering of luminous energy is small. When the width of the partitioning wall member 1d is determined to be w, the propagation angle is determined to be θ and the thickness of the optical waveguide 1 is determined to be t, a rate of luminous energy losses due to the partitioning wall member 1d becomes w/(2t·tan θ). Therefore, the lowering of luminous energy of fluorescent light is sufficiently decreased by determining the width of the partitioning wall member 1d narrower and the thickness of the optical waveguide 1 greater. Further, in this embodiment, the exciting light is outgone from an end edge section of the slab-type optical waveguide 1 which end edge section is an end edge section in the propagating direction of the exciting light, so that noise generation due to passing through many places of the exciting light is suppressed.

EIGHTH EMBODIMENT

Figure 18:
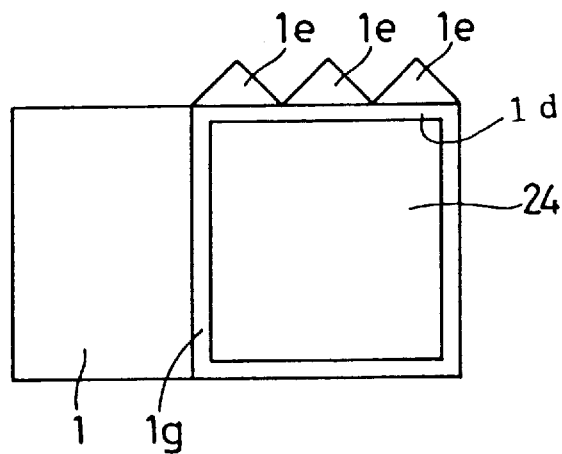
FIG. 18 is a plan view schematically illustrating a further embodiment of an optical measurement apparatus according to the present invention.

FIG. 18 is a plan view schematically illustrating an optical measurement apparatus of a still further embodiment according to the present invention. This embodiment differs from the embodiment illustrated in FIG. 15 in that three rectangular total reflection prisms 1e are provided in a continued condition instead of the rectangular total reflection prism 1c.

In this embodiment, a shifting quantity of an optical axis of fluorescent light within each rectangular total reflection prism 1e so that propsagating distance of the fluorescent light is shortened. Therefore, the luminous energy of the fluorescent light which is detected by the fluorescent light detector, is increased.

NINTH EMBODIMENT

Figure 19:
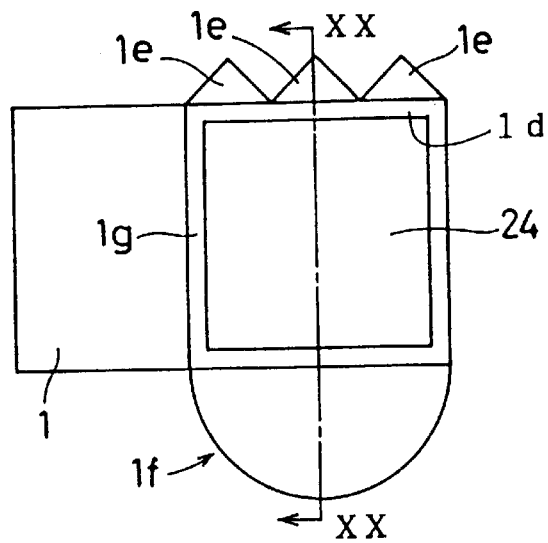
FIG. 19 is a plan view illustrating a yet further embodiment of an optical measurement apparatus according to the present invention.
Figure 20:
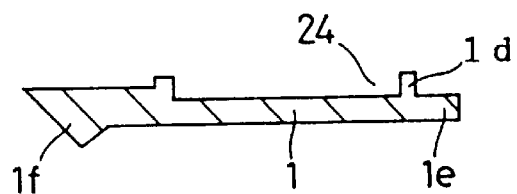
FIG. 20 is a cross sectional view taken along a line XX—XX in FIG. 19.

FIG. 19 is a plan view schematically illustrating an optical measurement apparatus of a still further embpodiment according to the present invention, while FIG. 20i a cross sectional view taken along a line XX—XX in FIG. 19. This embodiment differs from the embodiment illustrated in FIG. 18 in that a fluorescent light collecting lens If is further provided to the slab-type optical waveguide 1 at a side which is opposite to the rectangular total reflection prism 1e, that is at a fluorescent light outgoing edge. The fluorescent light collecting lens If has a plan shape which is projected in an arc shape, and has a side shape which is a tapered shape in its bottom portion so that the bottom portion approaches the rectangular total reflection prism side.

Therefore, in this embodiment, the fluorescent light outgone from the slab-type optical waveguide 1 is converged by the fluorescent light converging lens 1f to some degree, so that load of a fluorescent light converging lens which is included within a fluorescent light converging optical system is lightened. That is, a degree of convergence by the converging lens which is included within the fluorescent light converging optical system, is determined to be smaller.

Table 1 represents measured luminous energy os fluorescent light which are measured by the optical measurement apparatus illustrated in FIGS. 15, 18 and 19, respectively. Material of the slab-type optical waveguide 1 is polystyrene (refractive index is 1.58). Among fluorescent light which outgoes from the slab-type optical waveguide 1 and incidents in the fluorescent light converging optical system having a numerical aperture of F2, fluorescent light which reaches directly to the fluorescent light outgoing section of the slab-type optical waveguide 1 is represented as a direct fluorescent light component, and fluorescent light which reaches to the fluorescent light outgoing section of the slab-type optical waveguide 1 after being reflected by the rectangular total reflection prism 1e is represented as a reflection fluorescent light component. Further, a ratio of longitudinal and lateral lengthes of the reaction vessel, a distance between the reaction vessel and the fluorescent light detector, and a width of the fluorescent light detector is determined to be 1:1:1:1. Furthermore, numerical values within the table are calculated by a ray tracing method and by a numerical calculation, and unit of each numerical value is an arbitrary unit. Further, the optical measurement apparatus is not exactly the same to that of FIG. 18, and has an arrangement so that five rectangular total reflection prisms are provided.

TABLE 1

|  | Optical Measurement Apparatus In FIG. 15 | Optical Measurement Apparatus In FIG. 18 | Optical Measurement Apparatus In FIG. 19 |
| --- | --- | --- | --- |
| direct fluorescent light component | 6.78 | 6.78 | 9.16 |
| reflection fluorescent light component | 2.35 | 3.75 | 4.40 |
| sum | 9.13 | 10.53 | 13.56 |

As is apparent from table 1, luminous energy of fluorescent light which is obtained by single fluorescent light detector is increased by about 30–50% by prividing one or more rectangular total reflection prisms.

Further, the reflection fluorescent light component which is obtained by the optical measurement apparatus in FIG. 18 is greater than the reflection fluorescent light component which is obtained by the optical measurement apparatus in FIG. 15. The reason is that five rectangular prisms are provided so that a propagating distance of the reflection fluorescent light is shortened. Furthermore, the direct fluorescent light component and the reflection fluorescent light component which are obtained by the optical measurement apparatus in FIG. 19 is greater than the direct fluorescent light component and the reflection fluorescent light component which are obtained by the optical measurement apparatus in FIG. 18. The reason is that both fluorescent light component are converged by the fluorescent light converging lens.

TENTH EMBODIMENT

Figure 21:
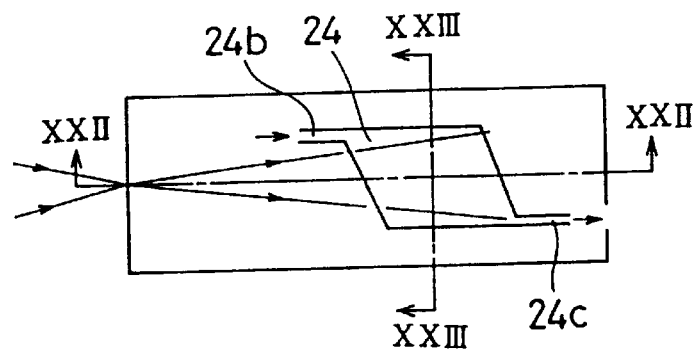
FIG. 21 is a plan view illustrating a still further embodiment of an optical measurement apparatus according to the present invention.
Figure 22:
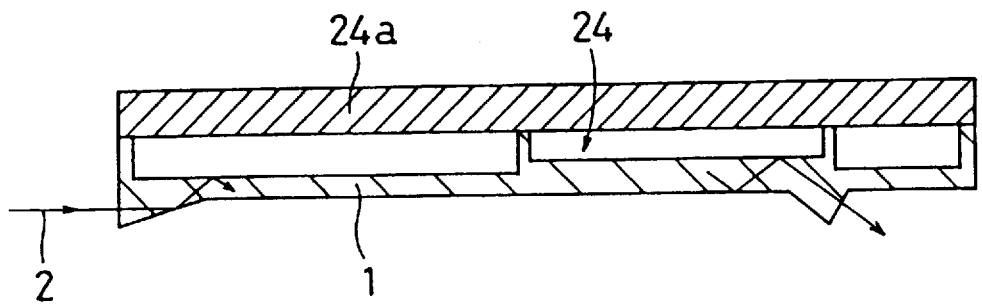
FIG. 22 is a cross sectional view taken along a line XXII—XXII in FIG. 21.
Figure 23:
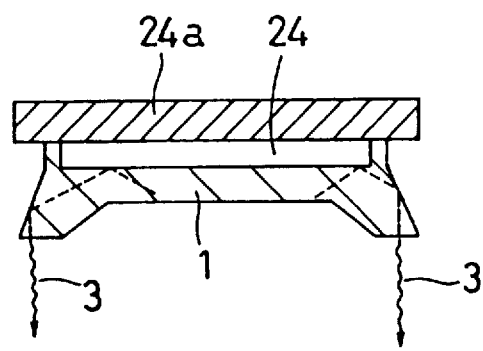
FIG. 23 is a cross sectional view taken along a line XXIII—XXIII in FIG. 21.
Figure 24:
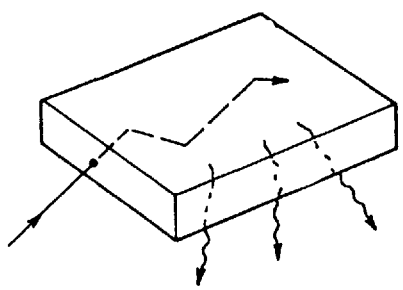
FIG. 24 is a perspective view useful in understanding a principle of a conventional method.

FIG. 21 is a plan view schematically illustrating an optical measurement apparatus of a still further embodiment according to the present invention, FIG. 22 is a cross sectional view taken along a line XXII—XXII in FIG. 21, and FIG. 23 is a cross sectional view taken along a line XXIII—XXIII in FIG. 21.

In this embodiment, a plan shape of the reaction vessel 24 is determined to be a parallelogram shape, and liquid supplying section 24b and liquid discharging section 24c are provided so that liquid is smoothly supplied and smoothly discharged. That is, the reaction vessel 24 is constructed as a flow cell. An ellipse shape, a deformed hexagon shape (for example, a compressedly deformed hexagon shape) and the like may be employed instead of the parallelogram shape. Further, total reflection prisms are employed as coupling prisms which are provided at the exciting light incidenting section and exciting light outgoing section of the slab-type optical waveguide, but, refraction prisms may be employed instead of the total reflection prisms. Further, no prisms may be formed at the exciting light incidenting section and the exciting light may directly be incodent in the slab-type optical waveguide. Furthermore, prisms are formed at the fluorescent light outgoing section which prisms are total reflection type and outgo the fluorescent light downward from the optical waveguide 1 which fluorescent light is to be radiated in directions which are opposite to one another. Rectangular total reflection prisms may be employed as is illustrated in FIGS. 15, 18 and 19, and fluorescent light converging lenses may be provided when they are required. Further, in this embodiment, The thickness of the optical waveguide 1 is determined to be a greater thickness only at its central portion, and the exciting light is outgone from the end edge section of the central portion which is determined its thickness to be greater thickness, as is illustrated in FIG. 21. The end edge section of the optical waveguide may be determined to be a more greater thickness so that the exciting light is outgone from the most end edge section of the optical waveguide 1.

INDUSTRIAL UTILIZING POSSIBILITY

The present invention is preferably applied to a measurement apparatus in which a reaction vessel is formed in one body with a slab-type optical waveguide. The measurement apparatus pours a test liquid and a reagent within the reaction vessel and introduces an exciting light within the slab-type optical waveguide so that optical characteristics in vicinity of a surface of the slab-type optical waveguide is measured. Sensitivity and accuracy in optical measurement is improved by lowering influence of stray light.

What is claimed is:

1. A method of measuring fluorescent compounds bound near the surface of an optical waveguide comprising:

introducing an exciting light into an optical waveguide, propagating the exciting light along a first direction within the waveguide in a totally reflective manner so as to generate an evanescent wave component, exciting a fluorescent compound bound near a surface of the waveguide with the evanescent wave component so as to radiate a fluorescent light wherein at least a portion of the fluorescent light enters the waveguide, propagating the fluorescent light that has entered the waveguide within the waveguide in a totally reflective manner wherein at least a portion of the fluorescent light propagated within the waveguide is output from the waveguide along a second direction which is at an angle to the first direction, measuring the amount of fluorescent light that is output from the waveguide with a detector, and correlating the amount of fluorescent light measured to the quantity of fluorescent compound.

2. The optical measurement method according to claim 1 wherein the optical waveguide has a first region wherein fluorescent compounds bound near the surface are excited by exciting light of greater energy and a second region wherein fluorescent compounds bound near the surface are excited by exciting light of lower energy, the method further comprising, screening the fluorescent light radiated from the first region from the detector such that only fluorescent light radiated from the second region is measured by the detector.

3. The method according to claim 1 wherein the angle is substantially 90°.

4. A method of measuring fluorescent compounds bound near the surface of a totally reflecting prism comprising:

introducing an exciting light into a totally reflective prism, propagating the exciting light along a first axis within the prism in a totally reflective manner so as to generate an evanescent wave component, exciting a fluorescent compound bound near a surface of the prism with the evanescent wave component so as to radiate a fluorescent light wherein at least a portion of the fluorescent light enters the prism, propagating the fluorescent light that has entered the prism within the prism in a totally reflective manner wherein at least a portion of the fluorescent light propagated within the prism is output from the prism along a second axis which is at an angle to the first axis, measuring the amount of fluorescent light that is output from the prism with a detector and correlating the amount of fluorescent light measured to the quantity of fluorescent compound.

5. An optical measurement apparatus comprising;

an exciting light source, means for binding compounds, a totally reflecting prism with a surface and with the means for binding compounds fixed to at least a portion of the surface, wherein the prism is capable of propagating the exciting light along a first axis within the prism in a totally reflective manner so as to generate an evanescent wave component in order to excite a fluorescent compound bound near a surface of the prism by the means for binding compounds with the evanescent wave component so as to cause the fluorescent compound to radiate a fluorescent light and allow at least a portion of the radiated fluorescent light to enter the prism and propagate within the prism in a totally reflective manner wherein at least a portion of the fluorescent light propagated within the prism is output from the prism along a second axis which is at an angle to the first axis, and a detector with a viewfield for detecting the fluorescent light which is output from the prism and enters the viewfield of the detector.

6. An optical measurement apparatus comprising;

an exciting light source, means for binding compounds, an optical waveguide with a surface and with the means for binding compounds fixed to at least a portion of the surface, wherein the waveguide is capable of propagating the exciting light along a first direction within the prism in a totally reflective manner so as to generate an evanescent wave component in order to excite a fluorescent compound bound near a surface of the waveguide by the means for binding compounds with the evanescent wave component so as to cause the fluorescent compound to radiate a fluorescent light and allow at least a portion of the radiated fluorescent light to enter the waveguide and propagate within the waveguide in a totally reflective manner wherein at least a portion of the fluorescent light propagated within the waveguide is output from the waveguide along a second direction which is at an angle to the first direction, and a detector with a viewfield for detecting the fluorescent light which is output from the waveguide and enters the viewfield.

7. The optical measuring apparatus according to claim 6 wherein the optical waveguide has a first region wherein fluorescent compounds bound near the surface by the means for binding compounds are excited by exciting light of greater energy and a second region wherein fluorescent compounds bound near the surface by the means for binding compounds are excited by exciting light of lower energy, and the fluorescent light radiated from the first region is screened from the viewfield of the detector such that only fluorescent light radiated from the second region enters the viewfield of the detector.

8. The optical measuring apparatus according to claim 6 wherein the optical waveguide has a lengthened portion, a reaction vessel portion and a minimum propagation angle, $\theta_{min}$, the reaction vessel portion being thicker than the lengthened portion and by an amount, $\Delta t$, wherein the lengthened portion is adjacent to the reaction vessel portion, the apparatus further comprising;

a reaction vessel formed from a plurality of wall members and the reaction vessel portion of the optical waveguide wherein one wall member with a thickness, w, is formed between the lengthened portion and the reaction vessel portion and $\Delta t$ is greater than $w/\tan \theta_{min}$.

9. The optical measuring apparatus according to claim 8 wherein the optical waveguide has a first edge face through which the exciting light is introduced, a second edge face on which is formed a total reflection prism and a third edge face and through which at least a portion of the fluorescent light propagated within the waveguide is output and wherein the total reflection prism guides at least a portion of the fluorescent light out through the third edge face.

10. The optical measurement apparatus according to claim 9 wherein a plurality of total reflection prisms are formed on the second edge face and wherein the plurality of total reflection prisms guide at least a portion of the evanescent fluorescent light out through the third edge face.

11. The optical measuring apparatus according to claim 10 further comprising an arc-shaped lens formed on the third edge face wherein the arc-shaped lens collects the evanescent fluorescent light that is output through the third edge face.

12. The optical measurement apparatus of claim 11 wherein the angle is substantially 90°.

13. The optical measuring apparatus according to claim 8 wherein the optical waveguide has a first edge face through which the exciting light is introduced and at least a second edge face on which is formed a total reflection prism which guides at least a portion of the fluorescent light propagated within the waveguide out through the first edge face.

14. The optical measuring apparatus according to claim 13 further comprising an arc-shaped lens formed on the third edge face wherein the arc-shaped lens collects the evanescent fluorescent light that is output through the third edge face.

15. The optical measuring apparatus according to claim 6 wherein the optical waveguide has a first edge face through which the exciting light is introduced and at least a second edge face on which is formed a total reflection prism which guides at least a portion of the fluorescent light propagated within the waveguide out through the first edge face.

16. The optical measuring apparatus according to claim 6 wherein the optical waveguide has a first edge face through which the exciting light is introduced, a second edge face on which is formed a total reflection prism and a third edge face and through which at least a portion of the fluorescent light propagated within the waveguide is output and wherein the total reflection prism guides at least a portion of the fluorescent light out through the third edge face.

17. The optical measurement apparatus according to claim 16 wherein a plurality of total reflection prisms are formed on the second edge face and wherein the plurality of total reflection prisms guide at least a portion of the evanescent fluorescent light out through the third edge face.

18. The optical measuring apparatus according to claim 16 further comprising an arc-shaped lens formed on the third edge face wherein the arc-shaped lens collects the evanescent fluorescent light that is output through the third edge face.

19. The optical measurement apparatus of claim 6 wherein the angle is substantially 90°.

\* \* \* \* \*